(12) United States Patent
Orth

(10) Patent No.: US 11,654,269 B2
(45) Date of Patent: May 23, 2023

(54) MEDICAL DEVICES FOR FLUID DELIVERY AND METHODS OF USE AND MANUFACTURE

(71) Applicant: Encompass Vascular, Inc., San Jose, CA (US)

(72) Inventor: Jean C. Orth, Morgan Hill, CA (US)

(73) Assignee: Encompass Vascular, Inc., San Jose, CA (US)

( * ) Notice: Subject to any disclaimer, the term of this patent is extended or adjusted under 35 U.S.C. 154(b) by 0 days.

(21) Appl. No.: 17/930,000

(22) Filed: Sep. 6, 2022

(65) Prior Publication Data

US 2023/0001162 A1    Jan. 5, 2023

Related U.S. Application Data

(63) Continuation of application No. PCT/US2022/017068, filed on Feb. 18, 2022.

(Continued)

(51) Int. Cl.
| | | |
|---|---|---|
| *A61M 25/10* | (2013.01) | |
| *A61M 25/00* | (2006.01) | |
| *A61M 25/01* | (2006.01) | |

(52) U.S. Cl.
CPC ........ *A61M 25/10* (2013.01); *A61M 25/1002* (2013.01); *A61M 2025/0087* (2013.01);
(Continued)

(58) Field of Classification Search
CPC .......... A61M 25/10; A61M 2025/0087; A61M 2025/0093; A61M 2025/1043; A61M 2025/105; A61M 2025/1086
See application file for complete search history.

(56) References Cited

U.S. PATENT DOCUMENTS

| | | | |
|---|---|---|---|
| 4,693,243 A | * | 9/1987 | Buras ................ A61M 16/0486 604/103.01 |
| 4,782,834 A | | 11/1988 | Maguire et al. |

(Continued)

FOREIGN PATENT DOCUMENTS

| | | |
|---|---|---|
| EP | 1825824 B1 | 11/2009 |
| EP | 1339448 B1 | 2/2010 |

(Continued)

OTHER PUBLICATIONS

Orth; U.S. Appl. No. 17/929,949 entitled "Medical devices for fluid delivery and methods of use and manufacture," filed Sep. 6, 2022.

(Continued)

*Primary Examiner* — Kami A Bosworth
(74) *Attorney, Agent, or Firm* — Shay Glenn LLP; Thomas M. Zlogar

(57) ABSTRACT

Medical devices and methods for delivering fluid. The medical devices include one or more needles for delivering fluid. The methods may optionally include expanding an expandable member such as an inflatable member to expand an expandable scaffold outward toward a lumen wall. The methods may include delivering a first fluid out of one or more needles, and delivering a secondary fluid (which may be the same type of fluid as the first fluid, or a different type of fluid) from the device without delivering the secondary fluid through a needle.

9 Claims, 18 Drawing Sheets

Related U.S. Application Data

(60) Provisional application No. 63/152,420, filed on Feb. 23, 2021.

(52) U.S. Cl.
CPC ............... *A61M 2025/0183* (2013.01); *A61M 2025/105* (2013.01); *A61M 2025/1086* (2013.01); *A61M 2210/12* (2013.01)

(56) References Cited

U.S. PATENT DOCUMENTS

| | | | |
|---|---|---|---|
| 5,049,132 A | 9/1991 | Shaffer et al. | |
| 5,336,178 A | 8/1994 | Kaplan et al. | |
| 5,425,709 A | 6/1995 | Gambale | |
| 5,464,395 A | 11/1995 | Faxon et al. | |
| 5,562,620 A * | 10/1996 | Klein | A61M 25/104 604/509 |
| 5,681,281 A * | 10/1997 | Vigil | A61M 25/10 604/103.01 |
| 5,693,029 A | 12/1997 | Leonhardt | |
| 5,713,863 A | 2/1998 | Vigil et al. | |
| 5,772,629 A | 6/1998 | Kaplan | |
| 5,810,767 A * | 9/1998 | Klein | A61F 2/958 604/103.01 |
| 5,843,033 A | 12/1998 | Ropiak | |
| 6,159,196 A | 12/2000 | Ruiz | |
| 6,283,947 B1 | 9/2001 | Mirzaee | |
| 6,283,951 B1 | 9/2001 | Flaherty et al. | |
| 6,302,870 B1 | 10/2001 | Jacobsen et al. | |
| 6,599,267 B1 | 7/2003 | Ray et al. | |
| 6,625,486 B2 | 9/2003 | Lundkvist et al. | |
| 6,656,155 B2 | 12/2003 | Freyman | |
| 6,692,466 B1 | 2/2004 | Chow | |
| 6,808,518 B2 | 10/2004 | Wellman et al. | |
| 6,991,617 B2 | 1/2006 | Hektner et al. | |
| 7,273,469 B1 | 9/2007 | Chang et al. | |
| 7,419,497 B2 | 9/2008 | Muni et al. | |
| 7,569,032 B2 | 8/2009 | Naimark et al. | |
| 7,572,270 B2 | 8/2009 | Johnson | |
| 7,837,670 B2 | 11/2010 | Barath | |
| 7,850,644 B2 | 12/2010 | Gonzalez et al. | |
| 7,901,451 B2 | 3/2011 | Savage et al. | |
| 8,043,257 B2 | 10/2011 | Nguyen et al. | |
| 8,357,118 B2 | 1/2013 | Orr | |
| 8,439,867 B2 | 5/2013 | Staskin | |
| 8,579,956 B2 | 11/2013 | Hossainy | |
| 8,740,849 B1 | 6/2014 | Fischell et al. | |
| 9,056,185 B2 | 6/2015 | Fischell et al. | |
| 9,108,030 B2 | 8/2015 | Braga | |
| 9,131,983 B2 | 9/2015 | Fischell et al. | |
| 9,333,327 B2 | 5/2016 | Setliff, III et al. | |
| 9,339,630 B2 | 5/2016 | Cook et al. | |
| 9,370,644 B2 | 6/2016 | Rocha-Singh | |
| 9,393,386 B2 | 7/2016 | Schneider et al. | |
| 9,468,443 B2 | 10/2016 | Elgaard et al. | |
| 9,504,491 B2 | 11/2016 | Callas et al. | |
| 9,757,543 B2 | 9/2017 | Raghavan et al. | |
| 10,086,175 B2 | 10/2018 | Torres et al. | |
| 10,118,016 B2 | 11/2018 | Schwartz et al. | |
| 10,124,153 B2 | 11/2018 | Feig et al. | |
| 10,172,729 B2 | 1/2019 | Fulkerson et al. | |
| 10,350,392 B2 | 7/2019 | Fischell et al. | |
| 10,433,821 B2 | 10/2019 | Gunday et al. | |
| 10,589,070 B2 | 3/2020 | Herman et al. | |
| 10,653,442 B2 | 5/2020 | Anand et al. | |
| 10,765,838 B2 | 9/2020 | Nishio et al. | |
| 11,071,847 B1 | 7/2021 | Orth et al. | |
| 11,167,111 B1 | 11/2021 | Orth et al. | |
| 11,491,312 B2 | 11/2022 | Orth et al. | |
| 2003/0032929 A1 | 2/2003 | McGuckin | |
| 2004/0127475 A1 * | 7/2004 | New | A61K 31/56 604/500 |
| 2005/0137615 A1 | 6/2005 | Mapes et al. | |
| 2005/0203612 A1 | 9/2005 | Bhat et al. | |
| 2005/0261662 A1 | 11/2005 | Palasis et al. | |
| 2007/0213761 A1 * | 9/2007 | Murphy | A61F 2/958 606/194 |
| 2008/0051866 A1 | 2/2008 | Chen et al. | |
| 2010/0168714 A1 * | 7/2010 | Burke | A61M 25/1002 604/509 |
| 2011/0184384 A1 | 7/2011 | DaValian et al. | |
| 2012/0271277 A1 | 10/2012 | Fischell et al. | |
| 2013/0060229 A1 | 3/2013 | Herman et al. | |
| 2017/0007310 A1 | 1/2017 | Rajagopalan et al. | |
| 2017/0035990 A1 | 2/2017 | Swift | |
| 2017/0100141 A1 | 4/2017 | Morero et al. | |
| 2018/0193078 A1 | 7/2018 | Rajagopalan et al. | |
| 2020/0060723 A1 | 2/2020 | Walzman | |
| 2020/0060942 A1 | 2/2020 | Rajagopalan et al. | |
| 2020/0261693 A1 | 8/2020 | Walzman | |
| 2022/0088350 A1 | 3/2022 | Orth et al. | |
| 2022/0265292 A1 * | 8/2022 | Carpenter | A61M 25/1002 |

FOREIGN PATENT DOCUMENTS

| | | |
|---|---|---|
| EP | 2328650 B1 | 4/2016 |
| EP | 3192473 A1 | 7/2017 |
| EP | 265487481 | 4/2018 |
| EP | 3558424 A1 | 10/2019 |
| EP | 2838598 B1 | 1/2020 |
| EP | 306579981 | 1/2020 |
| WO | WO2021/133966 A1 | 7/2021 |
| WO | WO2022/232589 A1 | 11/2022 |

OTHER PUBLICATIONS

Thomas; Restenosis treatment; 16 pages; retrieved from the internet (https://web.archive.org/web/20210804122825/https://www.news-medical.net/health/Restenosis-Treatment.aspx) 16 pages; on Jul. 15, 2022.

Orth et al.; U.S. Appl. No. 17/937,287 entitled "Medical devices for fluid delivery and methods of use and manufacture," filed Sep. 30, 2022.

* cited by examiner

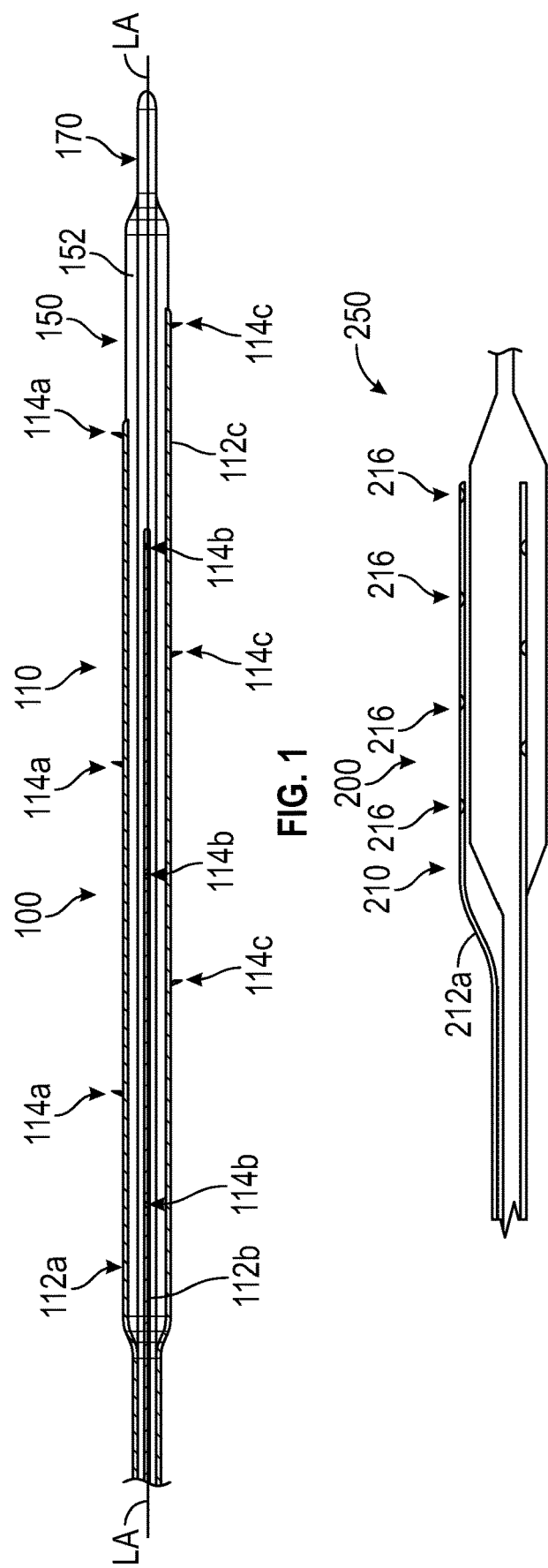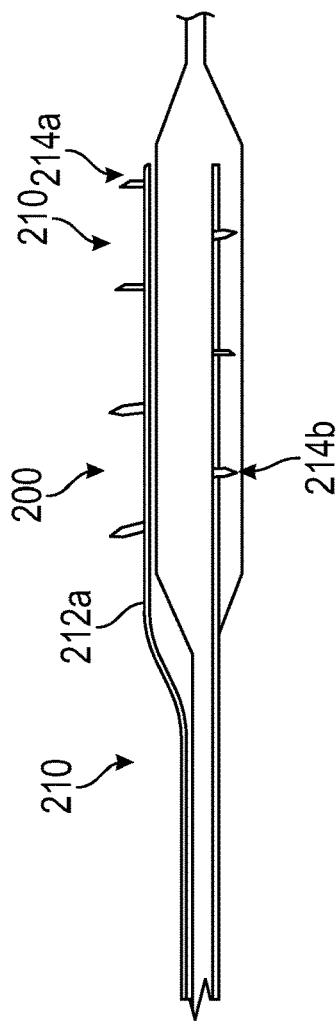
FIG. 1
FIG. 2A
FIG. 2B

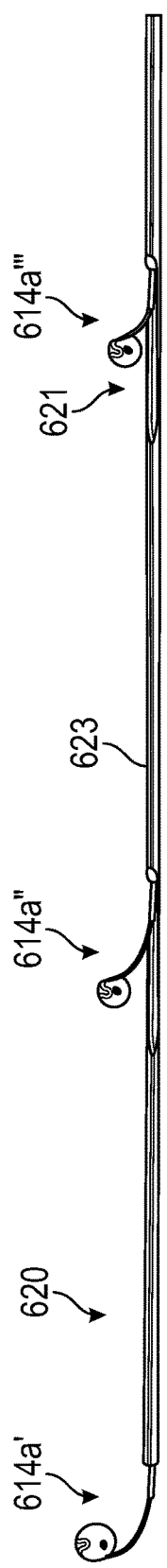
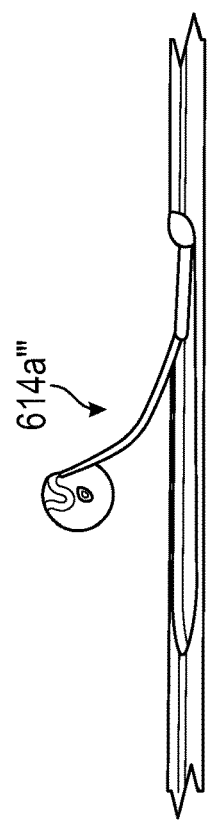
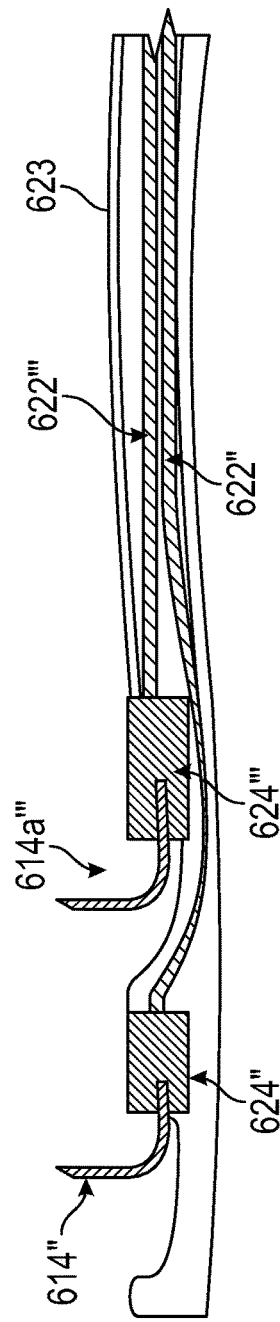

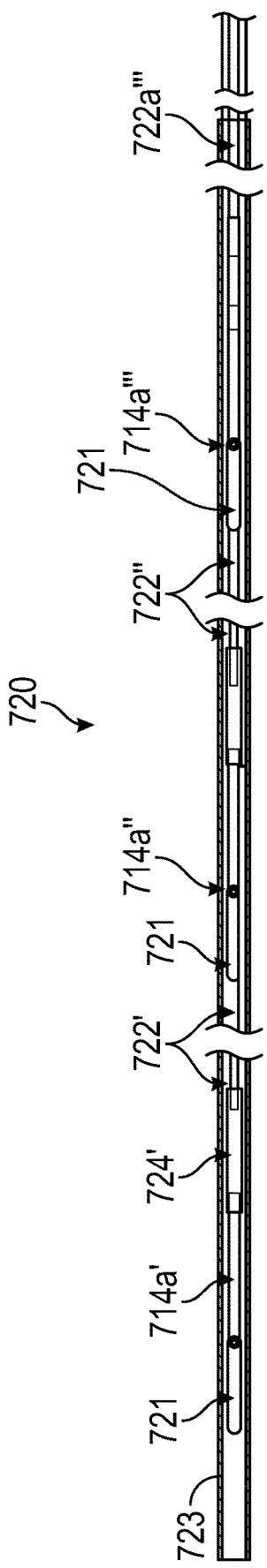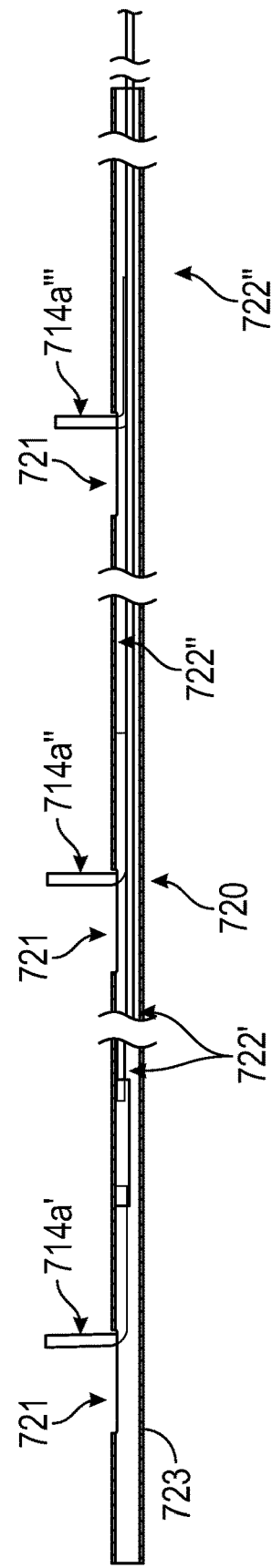
FIG. 7A
FIG. 7B

MEDICAL DEVICES FOR FLUID DELIVERY AND METHODS OF USE AND MANUFACTURE

CROSS REFERENCE TO RELATED APPLICATIONS

This application is a bypass continuation of International Application PCT/US2022/017068, filed Feb. 18, 2022, which claims priority to U.S. Prov. App. No. 63/152,420, filed Feb. 23, 2021, the entire disclosures of which are incorporated by reference herein for all purposes.

This application also incorporates by reference herein for all purposes the entire disclosure of U.S. Pat. No. 11,071,847, issued Jul. 27, 2021.

All publications and patent applications mentioned in this specification are herein incorporated by reference to the same extent as if each individual publication or patent application was specifically and individually indicated to be incorporated by reference.

FIELD

Intravascular (e.g., perivascular or adventitial) delivery of agents for the treatment of peripheral artery disease.

BACKGROUND

It is estimated that more than 20 million patients have peripheral artery disease (PAD), which can progress to critical limb ischemia (CLI), the most serious form of PAD.

Local luminal drug delivery with drug coated balloons (DCBs) and drug eluting stents (DES) have demonstrated some improvement in patency rates following above-the-knee revascularization, yet DCBs and DES have struggled to demonstrate improved patency following below-the-knee (BTK) interventions. A variety of causes for inconsistent results from DCB for the treatment of BTK PAD have been proposed by leaders in the field, such as: the high prevalence of intimal and medical calcification in BTK lesions that creates a physical barrier to effective drug penetration into the adventitia of the vessel, resulting in the inability to effectively inhibit a key contributor to the restenosis cascade; limited dosage from smaller drug-coated balloons; and wash-off of the drug from the balloon surface during device delivery to the target lesion site.

To address these limitations, recent attempts have been made at treating BTK PAD and CLI with an infusion catheter following primary angioplasty and/or primary atherectomy intervention. Yet inherent limitations remain with current infusion catheter systems, inclusive but not limited to, the use of a single infusion channel, single needle, and/or a fixed length single needle approach. Due to the limitations of existing infusion catheter systems, treating longer lesions can be time consuming, inherently user dependent, and inconsistent in coverage of the delivered therapy, both circumferentially and longitudinally along the length of the lesion.

Approaches are needed that address one or more of the deficiencies set forth above.

Additionally, it may be desirable to deliver one or more fluids to different depths of the vessel wall.

SUMMARY OF THE DISCLOSURE

This disclosure is related to intravascular delivery of agents for the treatment of peripheral artery disease.

One aspect of the disclosure is an intravascular apparatus adapted for delivery of a fluid.

In this aspect, the apparatus may comprise an inflatable balloon having an inflated cylindrical configuration.

In this aspect, the apparatus may comprise an expandable infusion scaffold comprising one or more primary spines disposed about an outer cylindrical surface of the inflatable balloon.

In this aspect, the one or more primary spines may comprise a plurality of primary radial openings therethrough, each of the plurality of primary radial openings associated with a needle that has a delivery configuration within a primary spine lumen of the primary spine in which a distal tip of the needle is radially constrained by the primary spine, and a deployed configuration in which the needle extends radially outward from the associated primary opening after the needle is advanced axially relative to the primary spine to facilitate delivery of a primary agent from the needle.

In this aspect, one or more primary spines may further comprise one or more secondary openings therethrough that are not associated with a needle and are not adapted to deploy a needle therefrom, and wherein the one or more secondary openings are in communication with the primary spine lumen to facilitate delivery of a secondary agent through the primary spine lumen and out of the one or more secondary openings.

In this aspect, the inflatable balloon may have a tapered proximal end and a tapered distal end, and wherein the cylindrical configuration of the balloon is in between the tapered proximal and distal ends. One or more primary spines may also be disposed about the optionally tapered proximal end.

In this aspect, one or more secondary openings may be circumferentially aligned with the plurality of primary openings.

In this aspect, one or more secondary openings in the associated primary spine may be circumferentially offset from the plurality of primary openings.

In this aspect, a first subset of secondary openings may be circumferentially aligned with the plurality of primary openings, and a second subset of secondary openings may be circumferentially offset from the plurality of primary openings.

In this aspect, one or more secondary openings may be axially offset from the plurality of primary openings.

In this aspect, one or more secondary openings may be axially aligned with and circumferentially offset from one of the plurality of primary openings.

In this aspect, the primary radial openings may also be in communication with the primary spine lumen to facilitate delivery of a secondary agent out of the one or more primary openings.

In this aspect, each of the plurality of primary openings may be larger than one or more secondary openings.

In this aspect, one or more secondary openings may be the same size as at least one of the plurality of primary openings.

In this aspect, a number of secondary openings may be different than or the same as the number of primary openings, optionally greater than the number of primary openings.

In this aspect, a plurality of secondary openings may be disposed axially in between first and second axially adjacent primary openings.

In this aspect, a plurality of needles associated with a primary spine may be adapted to be axially moved together as a unit relative to the associated primary spine, and may optionally be secured to a rail that is disposed within the primary spine. An inner surface of the primary spine and an outer surface of a rail may at least partially define a secondary agent pathway through which a secondary agent is delivered.

In this aspect, the plurality of needles may be adapted to be in communication with a first therapeutic agent source, and wherein a plurality of secondary openings may be adapted to be in communication with a second therapeutic agent source. First and second sources may include therein the same agent or different agents.

In this aspect, the plurality of needles and a plurality of secondary openings may be adapted to be in communication with the same agent source.

In this aspect, one or more secondary openings may comprise one or more discontinuities in a wall of the primary spine in the region of the primary spine that is disposed about the outer cylindrical surface of the balloon when inflated, wherein one or more discontinuities may be in communication with the primary spine lumen to facilitate delivery of the secondary agent through the one or more discontinuities in the primary spine. One or more discontinuities in the wall of the primary spine may comprise one or more laser-cut sections of the primary spine to facilitate weeping of the secondary agent through the laser cut sections of the primary spine when the secondary agent is delivered into and through the primary spine lumen. The primary spines may further comprise one or more discontinuities in the wall of the primary spine in a region of the primary spine that is proximal to the region that is disposed about the outer cylindrical surface of the balloon when inflated.

In this aspect, the expandable infusion scaffold may further comprise one or more secondary spines that are disposed about the outer cylindrical surface of the inflatable balloon, wherein the secondary spines each comprise one or more secondary openings therethrough that are not associated with a needle and are not adapted to deploy a needle therefrom, wherein the one or more secondary openings of the associated secondary spine are in communication with a secondary spine lumen to facilitate delivery of the secondary agent through the secondary spine lumen and out of the one or more secondary openings of the secondary spine.

In this aspect, the inflatable balloon may have a tapered proximal end and optionally tapered distal end, and wherein the cylindrical configuration is in between the tapered proximal and distal ends, and wherein one or more optional secondary spines are also disposed about the tapered proximal end.

The one or more optional secondary spines may be arranged helically about the cylindrical surface of the inflatable balloon.

The one or more optional secondary spines may be arranged axially about the cylindrical surface of the inflatable balloon.

In this aspect, at least two or more secondary openings of the one or more optional secondary spines may be circumferentially aligned.

In this aspect, at least two or more secondary openings of the one or more optional secondary spines may be circumferentially offset or axially offset.

In this aspect, at least two or more secondary openings of the one or more optional secondary spines may be axially aligned.

In this aspect, a subset of the one or more optional secondary openings may be arranged in an at least partial helical configuration.

In this aspect, one or more secondary openings in the one or more optional secondary may comprise one or more discontinuities in a wall of the secondary spine in the region of the secondary spine that is disposed about the outer cylindrical surface of the balloon when inflated, wherein the one or more discontinuities are in communication with the secondary spine lumen to facilitate delivery of the secondary agent through the one or more discontinuities in the secondary spine. One or more discontinuities in a wall of a secondary spine may comprise one or more laser-cut sections of the secondary spine to facilitate weeping of the secondary agent through the laser cut sections of the secondary spine when the secondary agent is delivered into and through the secondary spine lumen.

In this aspect, one or more primary spines may be arranged helically about the cylindrical surface of the inflatable balloon.

In this aspect, one or more primary spines may be arranged axially about the cylindrical surface of the inflatable balloon.

In this aspect, a plurality of needles associated with each of the one or more primary spines may be operatively coupled such that they are adapted to be moved axially as a group relative to the associated primary spine, optionally coupled to a rail within the primary spine. The optional rail may comprise a rail lumen that is in fluid communication with the plurality of needles.

In this aspect, each of the plurality of needles may be in fluid communication with a distinct fluid delivery lumen, which may optionally be in fluid communication with a rail lumen.

In this aspect, one or more primary spines may extend along at least half of the length of the portion of the balloon that has the inflated cylindrical configuration.

In this aspect, a portion of the balloon that has the inflated cylindrical configuration may have a length from 20 mm to 200 mm.

In this aspect, the expandable infusion scaffold may be attached to the inflatable balloon along at least a portion of a length of the scaffold.

In this aspect, the expandable infusion scaffold may not be attached to the inflatable balloon.

In this aspect, one or more primary spines may each have a stiffness that is not constant along the length of the inflatable member.

In this aspect, a plurality of needles may be operatively coupled to an axially moveable rail that is disposed within the associated primary spine lumen, and wherein the rail may have a stiffness that is not constant along the inflatable balloon.

In this aspect, one or more primary spines may comprise one or more of nitinol, stainless steel, polymer, polyimide, or a braided member.

One aspect of the disclosure is an intravascular apparatus adapted for delivery of a fluid. In this aspect, the apparatus may include an inflatable balloon having an inflated cylindrical configuration and an expandable infusion scaffold.

In this aspect, the expandable infusion scaffold may comprise one or more primary spines and/or one or more secondary spines, any of which may be disposed about an outer cylindrical surface of the inflatable balloon. In this aspect, the optional one or more primary spines may be any of the primary spines herein, and the optional one or more secondary spines may be any of the secondary spines herein.

One aspect of this disclosure is a method of intravascular fluid delivery and treatment.

In this aspect, the method may include advancing an intravascular apparatus to a target location within a vessel; inflating a balloon toward a cylindrical configuration to cause one or more primary spines of an expandable infusion scaffold to expand toward a vessel wall and be disposed about an outer cylindrical surface of the balloon; moving a plurality of needles axially within the one or more primary spines and deploying the plurality of needles out of radial primary openings of the primary spines such that tips of each of the plurality of needles pierce into the vessel wall; and delivering a primary fluid agent out of the plurality of needles and into the vessel wall. Delivering a primary fluid agent out of the plurality of needles and into the vessel wall may comprise delivering the primary fluid agent into at least one of the media and adventitia of the vessel wall.

In this aspect, the method may include delivering a secondary fluid agent out of one or more secondary openings to expose the vessel wall to the secondary fluid agent. The method may include delivering the secondary agent out of secondary openings that are in a primary spine and/or a secondary spine.

In this aspect, exposing a vessel wall to a secondary fluid agent may comprise exposing the intimal layer of the vessel wall to the secondary fluid agent, and optionally not exposing an adventitial layer to the secondary fluid agent. In some applications, however, the secondary fluid agent may passively infuse into the media and/or adventitia.

In this aspect, delivering a primary fluid agent may comprise delivering an anti-restenosis agent out of the plurality of needles into the vessel wall.

In this aspect, delivering a secondary fluid agent may comprise delivering an anti-recoil agent to expose the vessel wall to the anti-recoil agent.

In this aspect, the primary fluid agent may be the same as a secondary fluid agent.

In this aspect, delivering a secondary agent may be initiated before or subsequent to when a plurality of needles are deployed from a primary spine.

In this aspect, delivering a secondary agent may be initiated at a time prior to delivering a primary fluid agent out of a plurality of needles.

In this aspect, delivering a secondary agent may occur while the primary fluid agent is being delivered out of the plurality of needles.

In this aspect, delivering a secondary agent may be initiated at a time subsequent to delivering the primary fluid agent.

BRIEF DESCRIPTION OF THE DRAWINGS

FIG. 1 is a side view of a distal region of an exemplary infusion device including an expandable scaffold in an expanded configuration.

FIG. 2A is a side view of a distal region of an exemplary infusion device including an expandable scaffold in an expanded configuration.

FIG. 2B is a side view of a distal region of an exemplary infusion device from FIG. 2A with needles deployed from elongate spines of the scaffold.

FIGS. 6A, 6B, 6C and 6D illustrate views of portions of an exemplary needle subassembly or rail track subassembly.

FIG. 7A illustrates a top view of an exemplary needle or rail track subassembly.

FIG. 7B illustrates a side view of the exemplary needle or rail track subassembly from FIG. 7A.

DETAILED DESCRIPTION

Figure 3A:
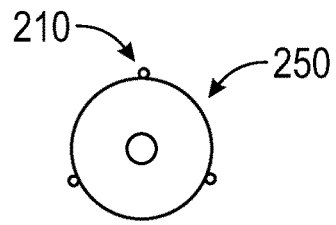
FIG. 3A is an end view of a distal region of an exemplary infusion device with an inflatable member inflated.

The disclosure herein is related to methods, devices and systems for the delivery of one or more therapeutic agents for the treatment of peripheral artery disease. The methods, devices and systems herein are adapted to efficiently and reliably deliver the desired dose of an agent to a target region of adventitial tissue, particularly compared to existing drug coated balloons (DCB), drug eluting stents (DES), and single-needle delivery devices. Additionally, the methods, devices and systems herein are also adapted to efficiently and reliably deliver the desired dose of an agent to a shallower depth in the vessel wall, such as to the intimal layer. When treating PAD, it may be beneficial to deliver first and second agents to different depths within the vessel wall for different therapeutic purposes. For example only, an anti-recoil therapeutic agent may be exposed to the vessel wall, optionally into the intima, to provide an anti-recoil therapy, while an anti-restenosis therapeutic agent may be delivered into the media and/or adventitia to provide an anti-restenosis therapy. A therapeutic agent delivered deeper into the vessel wall is generally referred to herein as a primary agent, while a therapeutic agent exposed to the vessel wall and delivered to a relatively shallower region of the vessel wall is generally referred to herein as a secondary agent.

Primary agents herein may comprise a single agent, or they may include more than one type of agent either combined or separate. Delivering primary agents out of the needles may include delivering more than one type of agent out of the needles in combination and simultaneously and/or delivering more than one type of agent separately. For example only, a primary agent may comprise first and second primary agents (or more), and wherein the first primary agent may be delivered before the second primary agent.

Similarly, secondary agents herein may comprise a single agent, or they may include more than one type of agent either combined or separate. Delivering secondary agents out of at least one of the secondary and primary openings may include delivering more than one type of agent out of the openings in combination and simultaneously and/or delivering more than one type of agent separately. For example only, a secondary agent may comprise first and second secondary agents (or more), and wherein the first secondary agent may be delivered before the second secondary agent.

Infusion devices herein may include a plurality of deployable needles, which are spaced axially (also referred to herein as longitudinally) and circumferentially apart around the infusion device, allowing more uniform circumferential coverage and a greater span of tissue along the lesion length to be targeted with a primary agent without having to move the infusion device within the vessel. It is of course understood that any of the treatments herein may include delivering a primary agent, after which the infusion device may be moved to a different location within the vessel before again delivering the same or a different primary agent, which is described above.

Additionally, infusion devices herein may be positioned against a vessel wall upon application of a radially outward force, which is generally described herein as a force applied by an inflatable member or balloon, although it is conceivable that non-inflatable members may alternatively be used. After the infusion device is apposed against the vessel wall, the needles can be deployed outward such that they pierce through the vessel wall and optionally into the adventitia layer of the vessel wall. Once the needles have been advanced into the wall and optionally into the adventitia, the desired therapeutic primary agent is delivered though the needles, out of the needles, and into the primary target tissue within the vessel wall. In some methods, the volume and rate of infusion may be controlled based on one or more of a desired lesion length and/or desired volume of agent infusion.

One or more of any of the following primary therapeutic agents or types of agents, including but not limited to any combination thereof, may be delivered from the infusion devices herein during any of the methods of use herein: antiplatelet agents; anti-inflammatory agents; antiproliferative drugs as referred to as cell-proliferation inhibitors; immunosuppressants such as mTOR and IMDH inhibitors; anticoagulation drugs; antithrombotic agents; lipid-lowering drugs; angiotensin-converting enzyme (ACE) inhibitors; regenerative agents; and stem cells. While the disclosure herein focuses on PAD, the device and systems herein may be used to treat alternative conditions, such as, for example only, chronic obstructive pulmonary disease ("COPD"), which is described in U.S. Prov. App. No. 62/953,342, which is incorporated by reference herein in this regard. Agents that may be delivered to treat COPD, for example, include but are not limited to anti-inflammatory agents, receptor antagonists, and neurotoxins.

The disclosure that follows describes non-limiting exemplary infusion devices that are adapted and configured to deliver one or more primary therapeutic agents and provide one or more of the advantages set forth herein, such as efficiently delivering a desired volume or dose to a target region of tissue in the vessel wall. While FIGS. 1-16 may illustrate examples of infusion devices that do not include secondary openings, it is understood that any suitable feature or aspect of FIGS. 1-16 and the disclosure that now follows may be incorporated into any apparatus and method of use herein that includes both primary openings and one or more secondary openings, whether those one or more secondary openings are disposed in a primary spine or an optional secondary spine. It is understood that any of the infusion spines in FIGS. 1-16 may be considered a primary infusion spine (or primary spine) even if not expressly referenced as a primary spine. It is also understood that certain disclosure that follows (with reference to FIGS. 1-16) that is generally related to a spine may, however, apply to secondary spines herein, and may be incorporated into any suitable secondary spine herein. For example, disclosure that follows related to a material that may be used for spines herein may be applicable to primary and/or secondary spines. Additionally, for example, disclosure that follows related to openings in a spine may also be applicable to any of the secondary spines herein.

In this disclosure, the phrases "primary spine" and "primary infusion spine" (or similar phrases) refer to infusion spines that include at least one primary opening from which a needle is deployed. Primary spines herein may also include one or more secondary openings (described in more detail below), wherein the one or more secondary openings are not associated with a needle and thus a needle is not and cannot be deployed from a secondary opening. In this disclosure, the phrases "secondary spine" and "secondary infusion spine" (or similar phrases) refer to infusion spines that do not include any primary openings from a which a needle can be deployed. Secondary spines herein thus include one or more secondary openings and do not include any primary openings.

FIG. 1 illustrates a distal region of an example of an infusion device. Infusion device 100 includes an expandable infusion scaffold 110 that includes at least first and second primary infusion spines 112a, 112b, and 112c (three shown in this example), which are shown in FIG. 1 in expanded configuration with the infusion needles deployed. Unless indicated herein to the contrary, the infusion spines herein may also be referred to as a plurality of infusion spines. Infusion spines (both primary spines and optional secondary spines) are sized, positioned, and configured to be expandable by a generally radially outward force, which in this example is applied by an inflatable member 150. Any of the inflatable members herein may include one or more of a compliant material (e.g., polyurethane or silicone), a non-compliant material (e.g., polyester or nylon), or a semi-compliant material. As shown, the primary infusion spines 112a, 112b and 112c are circumferentially spaced about an outer surface of the inflatable member 150 with a long axis (LA) of the infusion device when the primary spines are expanded. The long axis in this embodiment is also a long axis of the inflatable member 150. In this example, the primary spines are parallel (or substantially parallel) with the long axis of the infusion device 100 and the inflatable member 150 when expanded, as shown. As used herein, the phrase substantially parallel in this context includes slight deviations from being parallel and includes spines that have configurations that still facilitate the efficient and effective delivery of therapeutic agent to the desired tissue. One of skill in the art will appreciate that substantially parallel as used in this context allows for some deviation from strictly parallel, such as at an angle of five or ten degrees relative to a long axis, for example.

Any of the primary spines shown in FIGS. 1-2B may be replaced by an optional secondary spine, which are described elsewhere herein.

In this example the inflatable member has a cylindrical configuration when expanded, as shown. The term cylindrical as used in this context includes configurations that approximate a cylinder even if not perfectly cylindrical, which may be the case if a plurality of infusion spines are attached or engaging an outer surface of the inflatable member and the balloon does not have a perfectly cylindrical configuration when expanded. Additionally, an inflatable member may still be considered to have a cylindrical configuration even if the inflatable member has at least one end region that is tapered or has any other configuration that is not orthogonal with the long axis, such as the tapered distal and proximal ends of the inflatable member that are shown in FIG. 1. Additionally, for example, an inflatable member with a general dumbbell configuration may be considered to have a cylindrical configuration. Additionally still, when the description herein describes inflatable members having cylindrical configurations when expanded, it refers to the configuration the inflatable member would take after being expanded outside of a patient. This is meant to clarify that when expanded or inflated within a vessel of the patient, there may be one or more anatomical restrictions that prevent the inflatable member from transitioning to the cylindrical configuration it would assume if expanded outside of a patient, such as the configuration of the vessel wall in which the infusion device is placed. In both scenarios, the inflatable member in these examples is considered to have a cylindrical configuration when expanded.

The primary and optional secondary infusion spines herein may be connected (directly or indirectly) to the inflatable member, such as by bonding, adhesion, or using any other suitable technique for securing the spines to an inflatable member. In any of the examples herein, the spines may alternatively not be connected to the inflatable member, but they are still adapted to be expanded by inflation of the inflation member due to their proximity to the inflatable member. For example, the expandable infusion scaffold may be delivered on or over a balloon-based catheter in a compressed low-profile delivery state, and then expanded by dilating the balloon-based catheter at the intended location within the vessel.

Figure 11A:
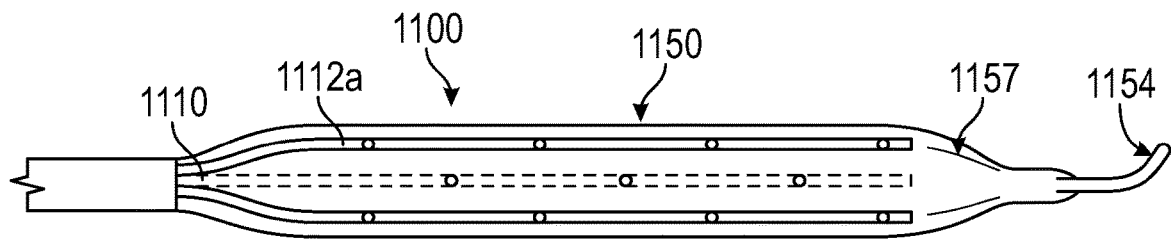
FIGS. 11A and 11B illustrate side and end views, respectively, of an exemplary infusion device in a collapsed lower profile delivery configuration.
Figure 11B:
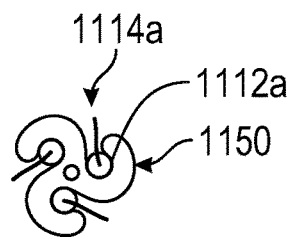
Figure 11C:
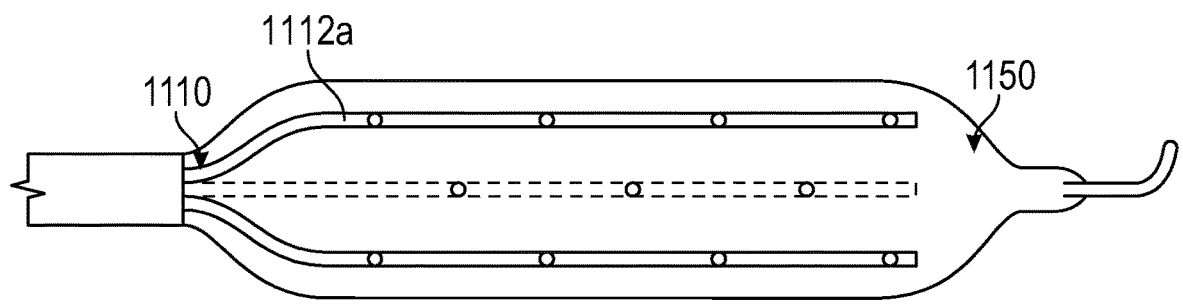
FIGS. 11C and 11D illustrate side and end views, respectively, of the exemplary infusion device from FIGS. 11A and 11B in an expanded configuration with needles deployed.

FIG. 1 shows an exemplary inflatable member 150 and an expandable infusion scaffold 110, both in an expanded state or configuration. For delivery, the expandable infusion scaffold is in a collapsed delivery configuration in which the primary infusion spines are closer to adjacent primary spines than in the expanded state, such as shown in FIG. 11A. It is understood that FIGS. 11A-11D are an alternative embodiment, and the reference to FIG. 11A is meant to illustrate an infusion scaffold in a collapsed delivery configuration (or at least a configuration in which it is not fully expanded). During delivery, the inflatable member is also in a lower profile unexpanded (and uninflated) collapsed delivery configuration. The internal volume of the inflatable member is also less in the delivery state than in the deployed state. Once the infusion device is delivered to the target location within a vessel, the inflatable member is inflated, which pressurizes the inflatable member. This expansion of the inflatable member causes the inflatable member to increase in a radial dimension and apply a force to the plurality of primary infusion spines that are disposed around the inflatable member. This causes the primary spines to expand radially and which also causes the relative circumferential distance between the primary spines to increase, an example of which is shown in FIG. 11C. The expandable infusion scaffold is thus expanded towards the vessel wall by inflating and expanding the inflatable member.

The inflatable member may have a variety of collapsed states or configurations. For example, the inflatable member may be folded in one or more locations to facilitate its collapse, while in other embodiments the inflatable member may not have a particular or well-defined collapsed state.

The inflatable members herein are sized and configured such that when expanded, the plurality of infusion spines (primary spines and optional secondary spines) will be moved radially outward and in contact or substantial contact with the vessel wall. It is understood that due to some variability in vessel wall size, some portion of any of the infusion spines may not make direct contact with vessel wall. The inflatable member may be sized such that it may have a deployed diameter that is larger than an intended vessel size to help ensure that the infusion spines are in contact or substantial contact with the vessel wall. Maintaining sufficient pressure in the inflatable member such that the infusion spines are in substantial contact with the vessel wall can help support the needles as they are deployed and pierce through the vessel wall, which is described in more detail below.

Any of the expandable scaffolds herein may have infusion spines (primary and optionally secondary) that are optionally equidistantly spaced apart along their lengths, an example of which is shown in FIG. 1. For example, two infusion spines may be spaced apart 180 degrees around the inflatable member when the scaffold and infusion spines are expanded. Alternatively, three infusion spines may be spaced apart 120 degrees around the inflatable member when the scaffold and infusion spines are expanded. Alternatively, four infusion spines may be spaced apart 90 degrees around the inflatable member when the infusion spines are expanded, and so forth. In the collapsed delivery state, the infusion spines of the scaffold can also have the same general relative relationship even though they are closer together and not spaced as far apart.

While equal spacing between spines may in some applications provide more complete delivery of an agent to target tissue around or in the vessel wall, in alternative examples the infusion spines may not all be equidistantly spaced apart around the inflatable member.

Figure 16:
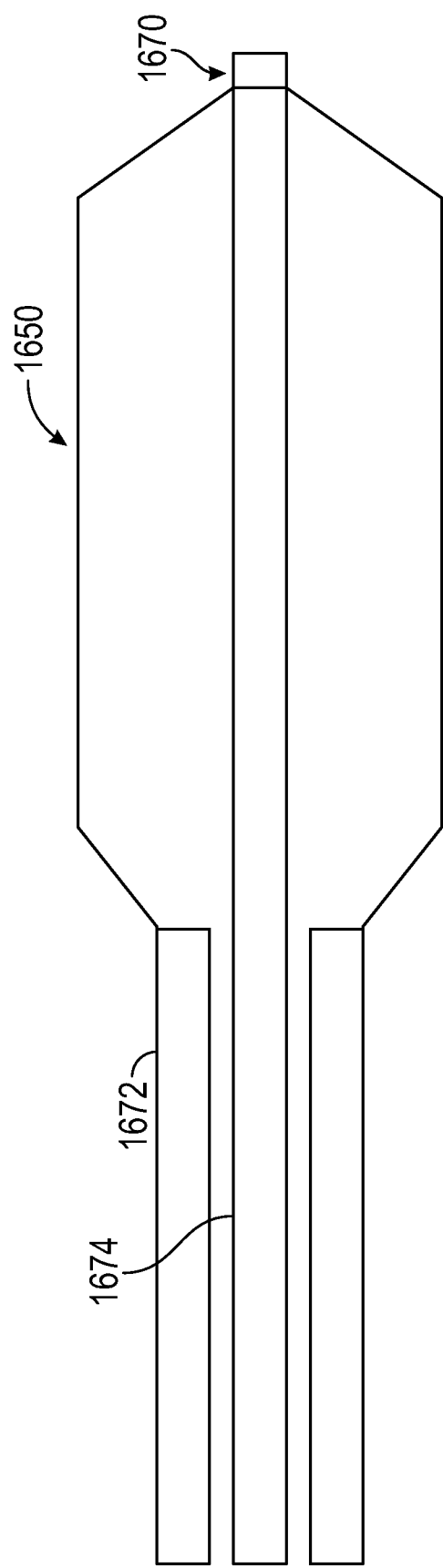
FIG. 16 is a side view illustrating an exemplary manner in which an inflatable member may be secured to a catheter shaft.

FIG. 16 illustrates a distal portion of an exemplary infusion device, wherein the expandable scaffold is not shown for clarity. In this example, the infusion device includes an inflatable member 1650, which is shown inflated. A distal end of inflatable member 1650 is coupled to inner shaft or member 1670, and a proximal end of inflatable member 1650 is coupled to outer shaft 1672. The inner and outer shafts 1670 and 1672 define therebetween inflation fluid pathway 1674, which is in fluid communication with an interior volume of inflatable member 1650. The inner volume of inflatable member 1650 and fluid pathway 1674 are in fluid communication with a fluid inflation port, such as inflation port 1333 or inflation port 1433 shown in FIGS. 13 and 14, and which are described in more detail below. Alternatively, the inflatable members herein may be secured to the infusion device in a manner that may be the same or similar to known balloon angioplasty catheters, examples of which are described in U.S. Pat. No. 4,782,834 and U.S. Ser. No. 10/086,175, and which are incorporated by reference herein for all purposes. Any of the fluid delivery devices herein that include one or more primary spines and optional secondary spines may include features shown in and described relative to FIG. 16.

Figure 5:
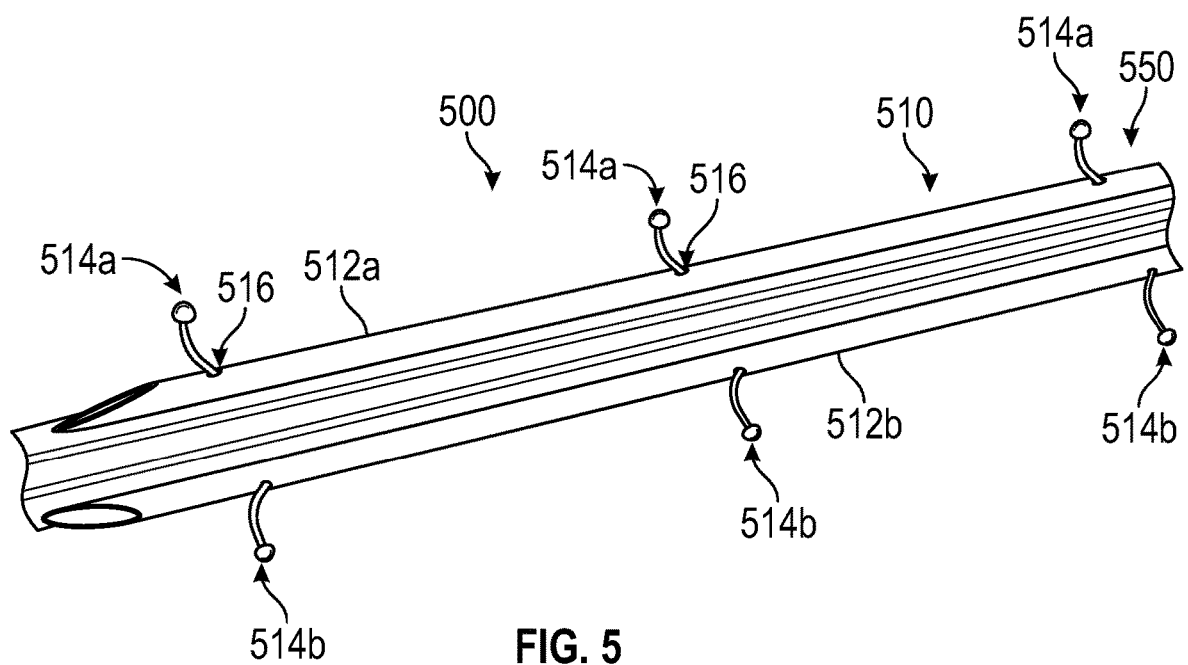
FIG. 5 is a distal region of an exemplary infusion device illustrating needles deployed from spines of an expandable scaffold.

Once the expandable inflation scaffold is expanded and in contact with (or at least substantially in contact with) or directly adjacent the vessel wall, each of a plurality of needles within a primary spine are deployed outward from a radial opening in the primary infusion spine, an example of which is labeled in FIG. 5 as opening 516. FIG. 1 illustrates a plurality of needles deployed from the expandable infusion scaffold, and in this example shows a plurality of needles deployed from each of the primary infusion spines. Needles 114a are shown deployed from primary infusion spine 112a. Needles 114b are shown deployed from primary infusion spine 112b. Needles 114c are shown deployed from primary infusion spine 112c. In this merely illustrative example, there are three needles shown deployed from each of the primary infusion spines. In any of the embodiments herein, each primary infusion spine may be associated with from two to fifty needles, all of which can be deployed from a radial opening in the primary spine. As used in this context, the term associated refers to needles that are within any particular primary spine in a delivery state, and are deployable from that particular primary spine to pierce the vessel wall.

When this disclosure refers to an infusion spine (primary and optional secondary), it is generally referring to one of the infusion spines of the expandable scaffold. Additionally, when a feature is described with respect to any particular or individual infusion spine, it is understood that all of the infusion spines of any particular scaffold may also have any or all of those features. The phrase infusion spine herein may be used interchangeably with the term spine.

The needles in any primary infusion spine herein are generally axially spaced apart, as shown in the examples of FIGS. 1, 2B and 5, for example. Spacing the needles axially apart can provide maximum coverage of the therapeutic agent along the length of the target lesion, which can increase the volume of tissue that may be targeted by using the infusion devices herein. Additionally, by having a plurality of primary infusion spines spaced around or about the device, with each infusion spine having a plurality of axially-spaced needles deployable therefrom, the infusion devices herein can ensure or increase the likelihood of delivering the agent to as much target tissue around the vessel as possible without having to rotate or move the infusion device to provide the desired circumferential coverage of the infused agent. It is of course understood that the infusion devices herein may also be moved in between episodes of agent delivery into the vessel wall. In these instances, the needles may be retracted, and the infusion device can be moved to a different location within the vessel or to a different vessel. The inflatable member and the scaffold are generally collapsed (at least partially) before moving the infusion device to a new location. It is also understood that devices herein may include a single primary spine, wherein a plurality of needles are associated with the single primary spine.

In any the infusion devices herein, any two axially spaced needles associated with a primary infusion spine may be spaced from 1 mm to 40 mm apart, such as from 5 mm to 35 mm apart, such as from 10 mm to 30 mm apart, such as from 15 mm to 20 mm apart.

In any of the infusion devices herein, any adjacent pair of three or more needles that are associated with a single primary infusion spine may be equidistantly spaced apart axially. Alternatively, any adjacent pair of three or more needles associated with a single primary infusion spine may not be equidistantly spaced apart axially. It is of course understood that any primary spine herein may only be associated with two needles, and this paragraph is only related to primary spines that may be associated with more than two needles.

In some illustrative embodiments, any of the infusion devices herein may include from six to 50 needles total. For example, an infusion device with three primary spines, each associated with two needles, would have six needles total.

FIG. 1 illustrates an example in which primary infusion spines do not have the same lengths and do not have distal ends that extend as far distally as at least one other distal end. In this example, the lengths of all of the primary spines that are shown are different, and none of their distal ends are axially aligned. In any of the infusion devices herein, any of the primary spines may have lengths that are the same such that their distal ends are axially aligned with any other spine distal end. In this context, the term length generally refers to the portion of the spine that overlaps with the inflatable member rather than a portion of a spine that may also extend proximally from the inflatable member.

The needles in different primary spines may or may not be axially aligned. For example, the exemplary needle placement in FIG. 1 shows none of the needles being axially aligned with needles in circumferentially adjacent primary spines. Any of the needles in the different primary infusion spines, however, may be axially aligned. Likewise, the primary infusion spines may also be axially aligned. For example, the infusion device may have rows of needles, with the rows spaced apart axially along the length of the infusion device, an example of which is shown in FIG. 5. A row as used in this context refers to two or more needles in different primary spines that are axially aligned. The apertures in the top and bottom spines in FIG. 11C are axially aligned, which will cause the needles associated with the top and bottom primary spines in FIG. 11C to be axially aligned when deployed.

In any of the infusion devices herein, the number of needles associated with each of the primary infusion spines may be the same. FIG. 1 shows an example of this, with three needles per primary infusion spine. In alternatives, the number of needles in each of the primary infusion spines may not be the same. For example, one primary spine may be associated with two needles, while a second primary spine may be associated with three needles. Any of the infusion devices herein may have an expandable scaffold with a plurality of primary spines, optionally wherein none of the primary spines has the same number of needles as any other primary spine.

Figure 4A:
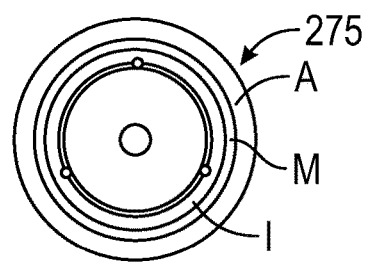
FIG. 4A is an end view of a distal region of the exemplary infusion device from FIG. 3A, shown within an exemplary vessel.
Figure 3B:
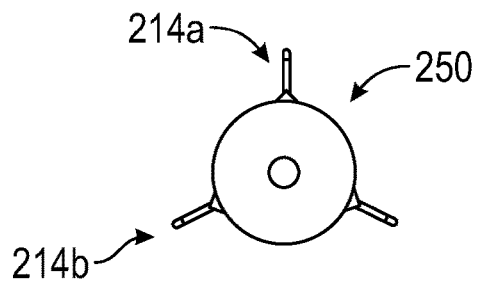
FIG. 3B is an end view of a distal region of the exemplary infusion device in FIG. 3A, shown with needles deployed.
Figure 4B:
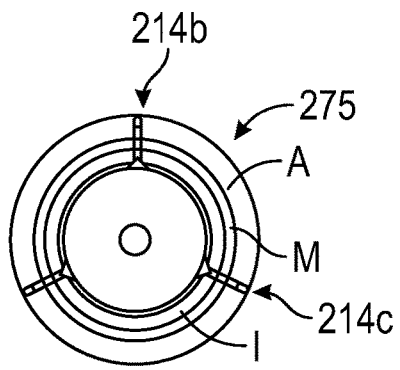
FIG. 4B is an end view of a distal region of the exemplary infusion device in FIG. 3A shown with needles deployed and within an exemplary vessel.

FIGS. 2A, 2B, 3A, 3B, 4A and 4B illustrate an exemplary infusion device 200 with an expandable infusion scaffold 210 that includes a plurality of primary infusion spines 212 (one labeled as 212a). Any suitable feature from FIG. 1 or described elsewhere herein may be incorporated into infusion device 200. Infusion device 200 also includes inflatable member 250 that when inflated and expanded causes the expandable infusion scaffold 210 to expand, described in more detail elsewhere herein. Each of the plurality of primary infusion spines includes a plurality of radial openings or windows 216 (shown in FIG. 2A), through which the plurality of needles 214 (labeled as 214a, 214b and 214c for the different spines) extend when deployed. FIGS. 2A (side view), 3A (end view) and 4A (end view in an exemplary vessel 275) show the infusion device after the inflatable member 250 has been inflated but with the needles not yet deployed, while FIGS. 2B, 3B and 4B show exemplary needles 214 deployed through the openings in the primary infusion spines 212. FIG. 4B illustrates the needles 214 piercing into (which may be referred to as "through") the vessel wall 275 and extending into the adventitia "A." FIGS. 4A and 4B illustrate intimal "I," medial "M," and adventitial "A" layers of the vessel. Any other disclosure herein from any other example may be incorporated into the examples in FIGS. 2A-4B. Any of the disclosure related to FIGS. 2A-4B may be incorporated by reference into suitable embodiments herein that include scaffolds with both primary and secondary openings.

Generally, the infusion spines herein include a lumen and a plurality of openings or windows therein, such as openings 216 in FIG. 2A. The needles herein are generally disposed within a primary infusion spine in a delivery state in which the needle tips are radially constrained by the spine, and are deployed from the primary infusion spine out of one of the needle openings in response to axial movement relative to the spine to pierce the vessel wall. The needles herein may be disposed within and deployed from the infusion spines in a variety of ways. Additionally, the needles herein may be in fluid communication with a fluid source in a variety of ways. The examples below are meant to be illustrative. The needles herein associated with a primary infusion spine may be deployable at the same time. The needles herein associated with an infusion spine may be deployable by moving them together as a unit, such as if they are coupled to a common axially movable member within the primary spine. The needles herein associated with a primary infusion spine may be separately deployable from within the primary spine.

Each of the plurality of needles associated with a primary infusion spine may be coupled to an axially moveable member that is disposed within the infusion spine, such that axial movement of the axially moveable member relative to the primary infusion spine causes the axial movement of the needle relative to the primary infusion spine.

In some embodiments herein, the needles associated with a primary infusion spine are all adapted to move together in unison upon the axial movement of an axially movable member, which may be referred to in this context as a common axially moveable member. In some alternatives, the needles associated with a primary infusion lumen (or primary spine lumen) may be axially moved independently from one another, such as when each needle is coupled to its own or individual axially moveable member within the primary spine.

In some embodiments the axially moveable member (which may be referred to as a rail or rail track) is a separate structure that does not specifically define a fluid lumen, although in these examples the axially moveable member may house therein one of more fluid lumens that are in fluid communication with one or more needles. Additionally, in these embodiments, one or more fluid lumens within the axially movable member may also be moved axially relative to the infusion spine in response to axial movement of the axially moveable member.

FIG. 5 illustrates an exemplary infusion device 500, which may incorporate any of the disclosure related to infusion device 100 shown in FIG. 1 or any other feature described herein. Infusion device 500 includes an expandable infusion scaffold 510, which includes a plurality of primary infusion spines 512a, 512b (a third infusion spine 512c is not visible in the side view of FIG. 5). The primary infusion spines 512a and 512b each include a plurality of openings 516 through which the needles are deployed. In this example, each of the primary spines is associated with three needles as shown, but more or fewer may be associated with each primary infusion spine as is described elsewhere herein.

Figure 6E:
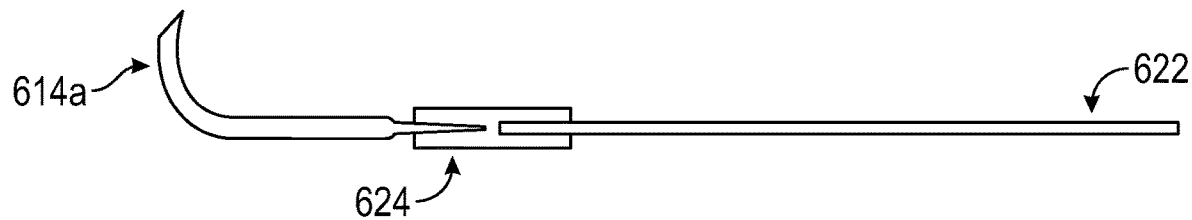
FIG. 6E illustrates an exemplary needle secured to a fluid delivery lumen.
Figure 6F:
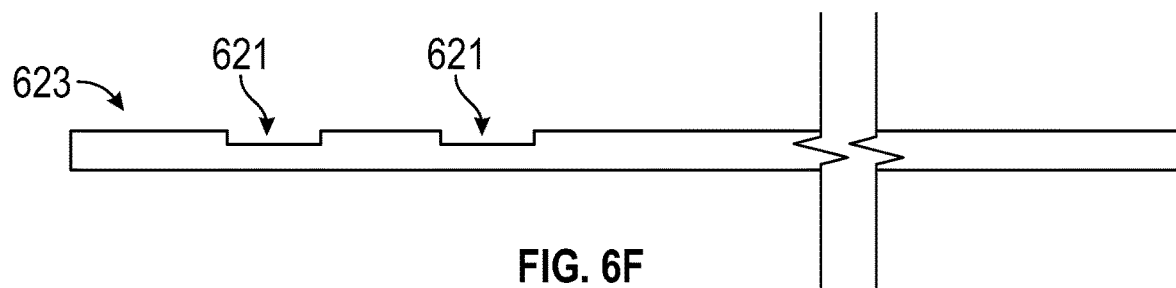
FIG. 6F illustrates an exemplary rail.
Figure 6G:
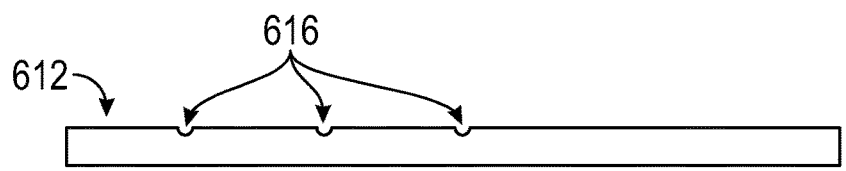
FIG. 6G illustrates a portion of an exemplary infusion spine.

FIGS. 6A-6F illustrates exemplary features of an exemplary needle subassembly 620 (any of which may be referred to herein as a rail track subassembly, and vice versa), with the primary infusion spine not shown for clarity. Rail track subassembly 620 is configured to both move the needles to deploy them from the primary infusion spine openings, as well as provide housing for one or more fluid lumens that are in fluid communication with one or more needles, and such fluid communication to the needles to deliver the agent into the vessel wall when the needles are deployed from the openings in the primary infusion spine. FIG. 6E illustrates an exemplary needle 614a coupled to fluid lumen 622 with an optional coupler 624. In other embodiments any of the needles herein may be directly connected to a fluid lumen. The needle 614a and fluid lumen 622, as shown in FIG. 6E, are then positioned within rail 623, which is shown alone in FIG. 6F. Rail 623 is an example of an axially movable member that is configured to be axially moved to cause the axial movement of a plurality of needles. Rail 623 is also sized and configured to house therein one or more fluid lumens, in this case fluid lumen 622″ and fluid lumen 622‴, as shown in FIG. 6D. As shown in FIG. 6D, in this example each needle is in fluid communication with a distinct or individual fluid lumen, but they are coupled to rail 623 such that they move axially together in unison when rail 623 is moved. With respect to FIG. 6E, each needle is coupled to an individual fluid lumen as shown, then advanced through rail 623 and coupled thereto, as is shown in FIGS. 6A-6D. FIG. 6D illustrates one example of a plurality of individual fluid lumens 622″ and 622‴ housed or disposed within a lumen of rail 623. Rail 623, at least in this exemplary embodiment, can be moved axially to axially move all of the needles, as well as serve to house the individual fluid lumens therein.

The needle subassembly 623 shown in FIG. 6A can be then positioned in one of the primary infusion spines, such as by front loading or back loading. When the needle subassembly 620 is loaded into a primary infusion spine, the needles will deflect radially inward towards the openings 621 that are labeled in FIG. 6F, and the needle subassembly may be positioned in the primary infusion spine such that the needles and needle tips are just proximal to the infusion spine openings 616 (with the needle tips radially constrained by an inner surface of the spine), labeled in the exemplary primary spine 612 shown in FIG. 6G.

Any of the needles herein may be formed with a natural bias towards a deployed configuration in which the needles extend at least partially radially outward, such as is shown in FIGS. 6A, 6B, 6C, 6D and 6E. When the needles are collapsed radially down or inward for delivery, they may or may not have a perfectly linear configuration due to their naturally biased and curved deployed configuration. When collapsed for delivery, any of the needles may retain a slight curvature in their configuration, with their tips radially constrained by the inner surface of the spine.

The use of the term rail herein does not necessarily impart any structural limitations. The rails herein may be elongate members that are sized and adapted to be moveable within an infusion lumen to facilitate the movement of one or more needles. Any of the rails herein may be a tubular member or partial tubular member, such as rail 623 shown in FIGS. 6A-6F, or any other elongate member (with or without a lumen) that is sized and configured for axial movement within a spine.

As part of an exemplary manufacturing of a rail track assembly, the needle and corresponding fluid lumen may be front-loaded through the rail. A coupler (e.g., 624" or 624'''), if used, may be secured (e.g., bonded, welded, or otherwise secured thereto) to the needle and fluid lumen as shown in FIG. 6E. The rail openings 621 may be formed by removing sections of the material of rail 623, which may itself be an elongate tubular member, such as a stainless steel or nitinol tubular member.

Each primary infusion spine in the exemplary infusion device shown in FIGS. 6A-6F is associated with at least three subcomponents or subassemblies—the infusion needle (s), the infusion lumen(s), and the rail track subassembly housing the respective infusion needle(s) and infusion lumen (s).

Any of the disclosure related to FIGS. 6A-6G may be incorporated by reference into any of the suitable disclosure herein related to devices and methods of use that includes scaffolds that comprise both primary and secondary openings.

In any of the examples herein, any of the fluid delivery lumens may have an outer diameter from 0.001 inches to 0.01 inches, for example. Fluid delivery lumens herein may also be referred to herein as fluid lumens.

In any of the examples herein, any of the axially moveable members (such as any of the rails) may have an outer diameter from 0.005 inches to 0.05 inches.

In any of the examples herein, any of the axially moveable members may have openings (e.g., openings 621) that are axially spaced from 5 mm to 80 mm apart, such as from 10 mm to 50 mm In any of the examples herein, any of the axially moveable members may have openings (e.g., openings 621) that have a length from 2 mm to 20 mm.

In any of the examples herein, any of the spines (primary spines and optional secondary spines) may have an outer diameter from 0.01 inches to 0.08 inches.

In any of the examples herein, any of the spines (primary spines and optional secondary spines) may have openings (e.g., openings 216, 516) that are axially spaced apart from 5 mm to 80 mm.

In any of the examples herein, any of the spines (primary spines and optional secondary spines) may have openings (e.g., openings 216, 516) may have openings with a diameter or length dimension from 0.05 mm to 10 mm.

FIGS. 7A and 7B, in top and side views, respectively, illustrate an exemplary rail track subassembly 720 (spine not shown for clarity), with three exemplary needles in deployed configurations. Any of the features from assembly 620 of FIG. 6A may be incorporated into assembly 720. Rail track subassembly 720 includes rail 723, which has openings 721 therethrough (only one of which is labeled in FIG. 7A), and in this example there are three openings 721 in rail 723. Needles 714a are coupled to individual and distinct fluid lumens 722, optionally via couplers 724 but alternatively directed connected thereto, which may be secured to rail 723 to secure the needle to the rail 723 and provide unitary axial movement of the needles 714 (which are individually labeled as 714a', 714a", and 714a''').

FIGS. 7A and 7B also illustrate how fluid lumens may extend through the rail 723 lumen. For example, fluid delivery lumen 722' is in fluid communication with needle 714a' and extends through rail 723. Fluid delivery lumen 722' extends adjacent to central needle 714a" and fluid delivery lumen 722", as shown in the central regions of FIGS. 7A and 7B. In the proximal region shown in FIGS. 7A and 7B, all three fluid delivery lumens 722', 722" and 722''' are adjacent one another within the rail 723. Any of the fluid delivery lumens herein may include a bend or deviation in its path such that it can pass next to a different needle and its associated fluid delivery lumen, which is shown in FIGS. 7A and 7B. In this manner, the needles can extend in the same direction from the primary spine, which can be seen in the top view of FIG. 7A. In the top view of FIG. 7A, the needles are all extending upward, or out of the page.

Any of the disclosure related to FIGS. 7A and 7B may be incorporated by reference into any of the suitable disclosure herein related to devices and methods of use that includes scaffolds that comprise both primary and secondary openings.

Figure 8:
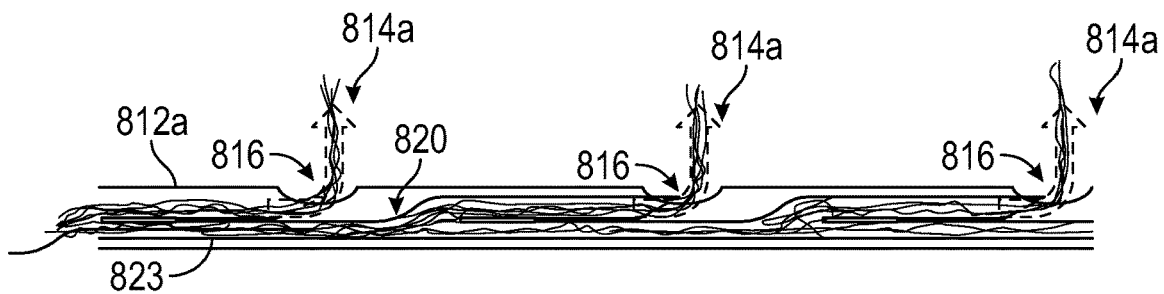
FIG. 8 is a side view of a plurality of exemplary needles deployed outward from an infusion spine.

In some embodiments, the axially movable member may also at least partially define a fluid lumen that is in fluid communication with one or more needles, such as in the example shown in FIG. 8. FIG. 8 illustrates an exemplary needle assembly 820 shown within an exemplary primary spine 812a, which includes top or radially outward openings 816. Needle assembly 820 is an axially movable member that in this embodiment also at least partially defines a fluid delivery lumen as shown that is in fluid communication with all of the needles 814a. Needles 814a are shown in their deployed configuration (tissue not shown for clarity) extending out of the spine openings 816. Any other feature from any other example herein may be incorporated into the features shown in FIG. 8, including use with any other inflatable member herein. Any of the disclosure related to FIG. 8 may be incorporated by reference into any of the suitable disclosure herein related to devices and methods of use that includes scaffolds that comprise both primary and secondary openings.

Figure 11D:
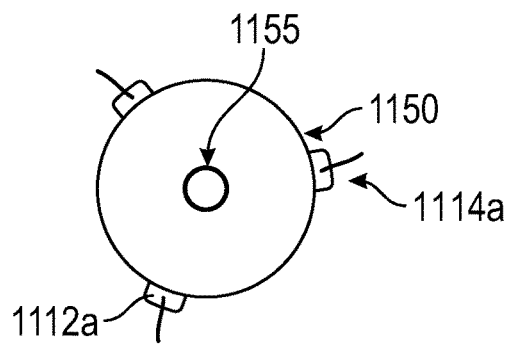

In some alternative embodiments, the needles may be extending from a primary infusion spine when the infusion device is in a collapsed delivery configuration. FIGS. 11A-11D illustrate such as example, with infusion device 1100 shown in a collapsed configuration in FIGS. 11A and 11B, and expanded in FIGS. 11C and 11D (the needles are shown only in FIGS. 11B and 11D for clarity). FIGS. 11A and 11C are side views, and FIGS. 11B and 11D are end views. As shown in FIG. 11B, needles 1114a are tucked within folded sections of inflatable member 1150 in the collapsed delivery state. Inflatable member 1150 may include sections of the material that are easier to fold to facilitate the predictable folding of the balloon around the primary infusion spines and needles, as shown in FIG. 11B. An exemplary guidewire 1154 disposed within guidewire lumen 1155 is also shown, which may be used to deliver any of the infusion devices herein using known guidewire delivery techniques and methods. FIGS. 11A and 11B also illustrate generally collapsed delivery configurations of spines and an inflatable member, which may be incorporated with any of the other examples herein wherein the needles are not deployed until the inflatable member is expanded. The inflatable members herein need not, however, collapse in a predictable manner as is shown in FIG. 11B.

Any of the disclosure related to FIGS. 11A-11D may be incorporated by reference into any of the suitable disclosure herein related to devices and methods of use that includes scaffolds that comprise both primary and secondary openings.

Any of the lumens herein (e.g., infusion spine lumen, rail lumen, and/or fluid lumen) may have or benefit from having one or more regions with sufficient flexibility to allow for the infusion device to be delivered to the target location in the vasculature. For example, any of the lumens herein may incorporate a tubular member having a wall with one or more regions with one or more discontinuities, such as cuts, therein (e.g., a laser cut or other technique) that imparts some degree of flexibility along at least a portion of its length. Discontinuities such as cuts made in a wall of any tubular member herein may be in the form of, for example without limitation, including combinations thereof, an at least partial spiral pattern, an at least partial brick pattern, or any other pattern that increases the flexibility of the wall of the lumen. More than one pattern may be implemented in the wall of any lumen (spine lumen, rail lumen, fluid delivery lumen, etc.), and the shape or configuration of a cut pattern may change along the length of the lumen. As is discussed elsewhere herein, discontinuities (e.g., laser cuts) in a wall of a primary or secondary spine may be considered as a secondary opening through which a secondary agent may be delivered to the vessel well.

Any of the fluid lumens herein may optionally include a non-permeable membrane on one or both of an inside or the outside, such as an elastomeric membrane (e.g., urethane, silicone, or hydrogel), which can prevent fluid from leaking therethrough. For example, any lumens that may include or more discontinuities (e.g., cuts) therein (e.g., laser cut tubes) may include one or more membranes secured thereto to maintain integrity.

Any of the lumens herein may comprise, for example, any combination of nitinol, stainless steel, polymer tubing, polyimide, braided tubing, or other structural material. Any of the lumens herein may be constructed to provide the desired fluid integrity and/or flexibility when being delivered to the target delivery site.

Figure 12:
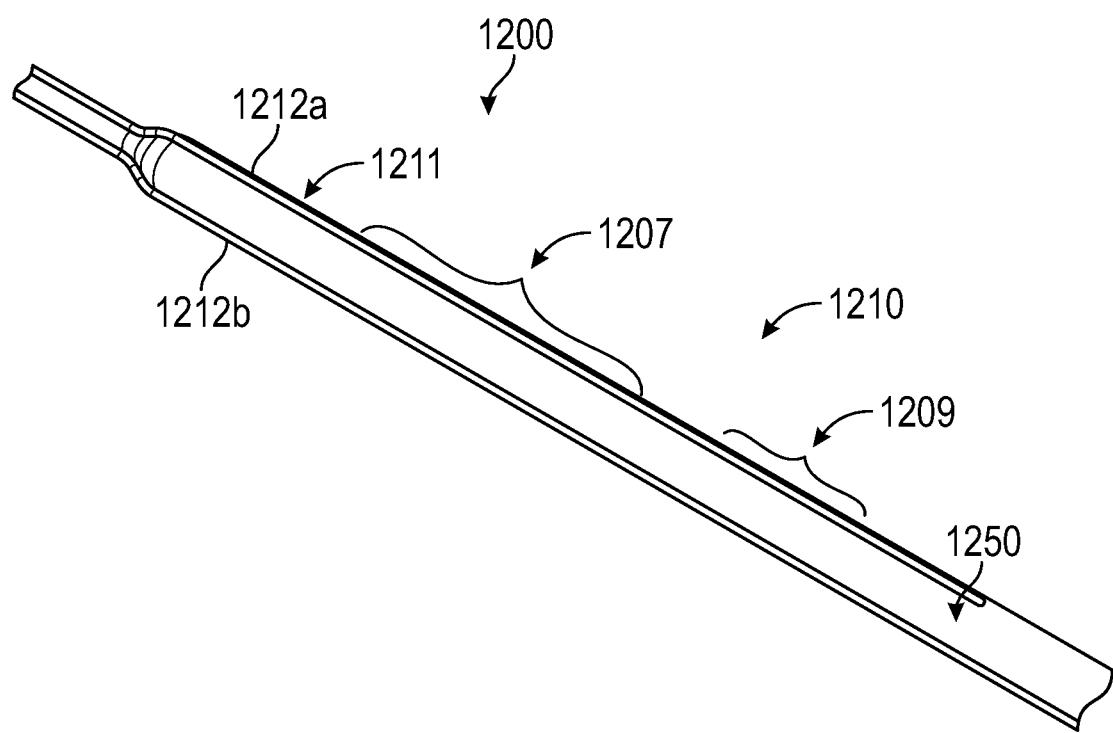
FIG. 12 illustrates a distal region of an exemplary infusion device in an expanded configuration, with regions that are more flexible than other sections of the spine.

In some examples, sections of primary infusion spine(s) in between needle regions may be more flexible to provide more flexibility at those locations, while the primary spine regions where the needles are deployed may have relatively higher stiffness to aid the needle piercing through tissue or calcifications. FIG. 12 illustrates an exemplary infusion device 1200, with inflatable member 1250 and scaffold 1210 in expanded configurations or states. Scaffold 1210 includes a plurality of primary spines 1212a and 1212b. Primary spine region 1207 may be configured to be more flexible than distal region 1209 and proximal region 1211 that are axially adjacent to region 1207. Needles may be present in regions 1209 and 1211, for example. Each primary spine may have a plurality of regions 1207 that are more flexible that other sections of the primary spine, any of which may be axially spaced apart with less flexible primary spine regions in between, which is described in more details with respect to FIG. 13. Any of the disclosure related to FIG. 12 may be incorporated by reference into any of the suitable disclosure herein related to devices and methods of use that includes scaffolds that comprise both primary and secondary openings.

Figure 13:
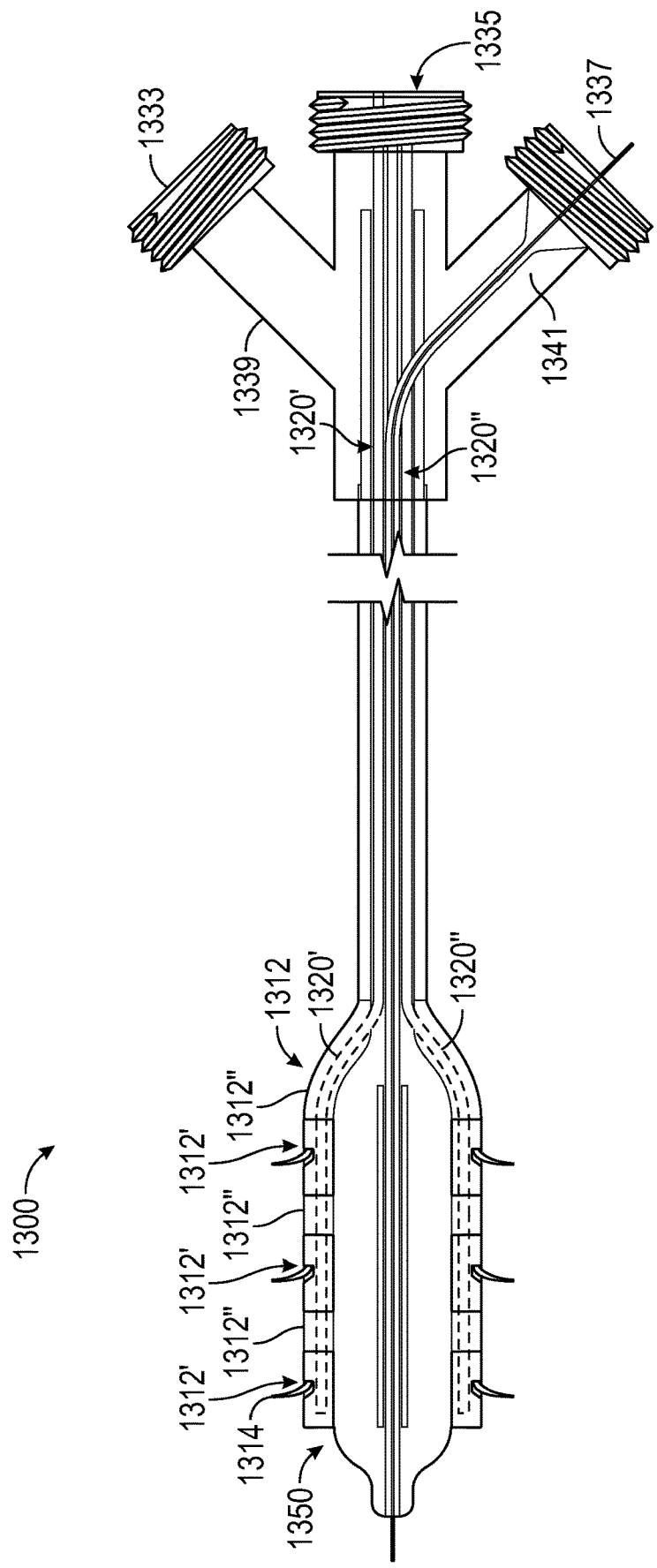
FIG. 13 is a side view illustrating an exemplary infusion device, including a proximal region positioned to be disposed outside of a patient.

FIG. 13 illustrates an exemplary infusion device 1300 shown with expandable member 1350 in an expanded configuration and a plurality of needles 1314 (only one of which is labeled) deployed from openings in primary spines 1312 (only one spine is labeled, and there may be additional spines and associated needles). In this example, the primary spines include first regions 1312' at and around the locations where needles extend through openings therefrom, and regions 1312" axially adjacent and optionally in between first regions 1312'. First regions 1312' may be considered to include the primary spine openings from which the needles extend. First regions 1312' may be less flexible than regions 1312". This arrangement may provide sufficient stiffness to the primary spine region where the needle extends therefrom, helping the needle pierce through tissue (or calcifications), while regions 1312" can provide more flexibility for tracking and delivery. Any of the primary spines herein may include first and second regions with different stiffness as in the example of FIG. 13.

As is set forth herein, the scaffold may or may not be attached to the inflatable member. In examples in which the scaffold (including the spines) is attached to the inflatable member, the spines (primary and optional secondary) may be secured to the inflatable member along their entire length, or less than their entire length. In some devices, the individual spines may be attached to the inflatable balloon at a plurality of axially spaced sections or regions along its length, and not directly attached to the inflatable member at one or more axially-spaced sections or regions along its length. For example only, with respect to FIG. 13, the plurality of spines may be attached to the inflatable member 1350 in regions 1312', but not attached directly to the inflatable member 1350 in regions 1312". Not directly attaching the spines to the inflatable member in regions 1312" may allow for more movement and flexibility in the more flexible regions 1312", which may provide more flexibility overall in the region of the scaffold, which can help when delivering the device. Any of the disclosure related to FIG. 13 may be incorporated by reference into any of the suitable disclosure herein related to devices and methods of use that includes scaffolds that comprise both primary and secondary openings.

FIG. 13 also illustrates exemplary rail track or needle subassemblies 1320' and 1320" within corresponding primary spines, which may include a plurality of needles and one or more fluid lumens, which are described in more detail herein (there may be as many subassemblies as there are spines).

FIG. 13 also illustrates an exemplary proximal region of infusion device 1300. The proximal region includes an adaptor 1339, which in this example is a three-port adaptor. Adaptor 1339 includes an inflation port 1333 configured to couple to a fluid delivery device (e.g., Inflation Device commonly used with dilatation catheters) to deliver an inflation fluid to inflate expandable member 1350. Adaptor 1339 also houses a guidewire lumen 1341 therein, which is sized and configured to receive guidewire 1337 therein, which may facilitate delivery of any of the infusion devices herein over a guidewire. Adaptor 1339 also includes an actuator coupling region 1335, which may be sized and configured to couple to an actuation member, an example of which is described in more detail with respect to FIG. 14.

Any other feature from any other infusion devices herein may be incorporated into the example in FIG. 13, and vice versa.

Figure 14:
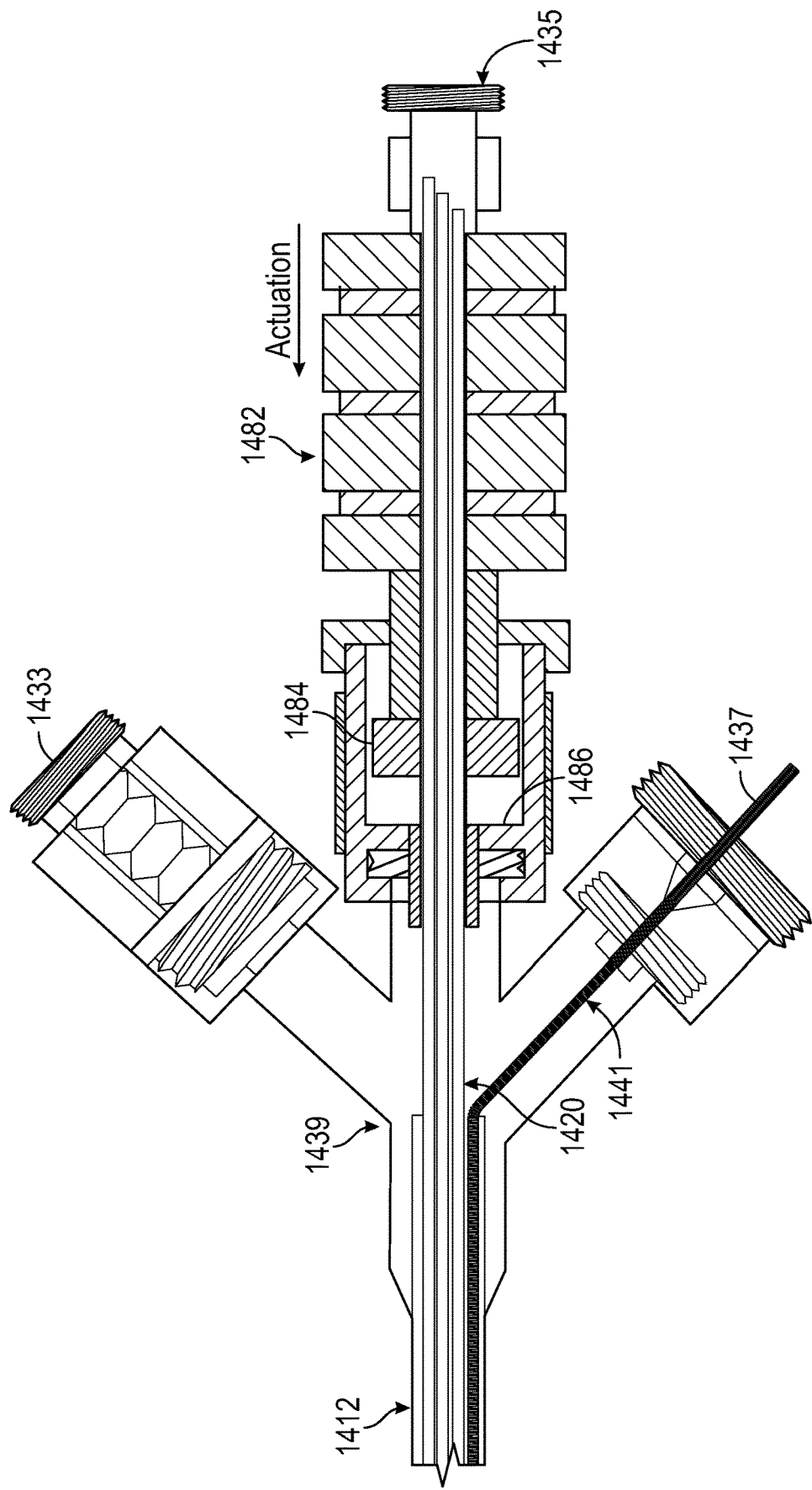
FIG. 14 is a side view of an exemplary proximal region of an exemplary infusion device, including an exemplary actuator.

FIG. 14 illustrates an exemplary proximal region of an infusion device, any features of which may be incorporated into any of the infusion devices herein, including those with scaffolds that include primary and secondary openings. The proximal region includes optionally three-port adaptor 1439, which may house a guidewire lumen 1441 therein that is adapted to receive a guidewire 1437 therein for guidewire delivery. In this example, the proximal handle region includes an actuator 1482 that is in operational communication with the rail track subassemblies to facilitate axial movement thereof, which are generally labeled 1420, but it is understand there may be two or more (such as the three that are shown). The rail track sub-assemblies 1420 may have proximal ends that are attached (directly or indirectly) to an inner surface of actuator 1482, such as by using any suitable bonding technique, which thereby causes the rail track subassemblies to move distally upon distal actuation of the actuator 1482, to thereby deploy the needles from the spine openings. In this example, actuator 1482 has a plunger type construction, with a distal member 1484 that is sized to interface with inner surface 1486 to stop further movement of the actuator 1482. This stop mechanism is an example of a stop mechanism that is adapted to control the distal travel of the actuator 1482. This can be set at any desired distance to control the amount of needle deployment. The proximal portion also includes infusion port 1435, which is adapted to be coupled to a source of therapeutic agent to facilitate delivery thereof through the one or more delivery lumens and to the needles. A proximal region of an exemplary spine 1412 is also shown in FIG. 14, but it is understood that there may be as many spines as there are rail track sub-assemblies. Any other feature from any other infusion devices herein may be incorporated into the example in FIG. 14, and vice versa.

Figure 15A:
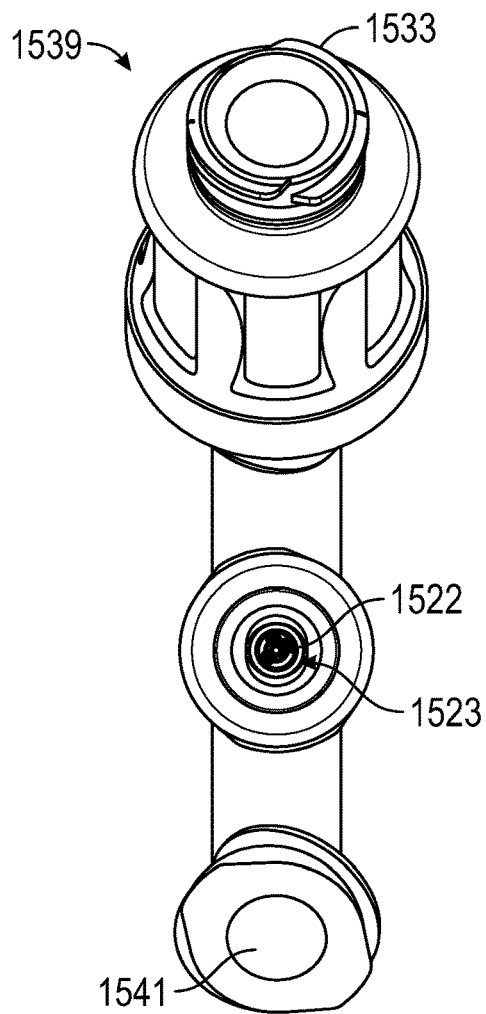
FIGS. 15A and 15B are proximal end views of a proximal external region of an exemplary infusion device.
Figure 15B:
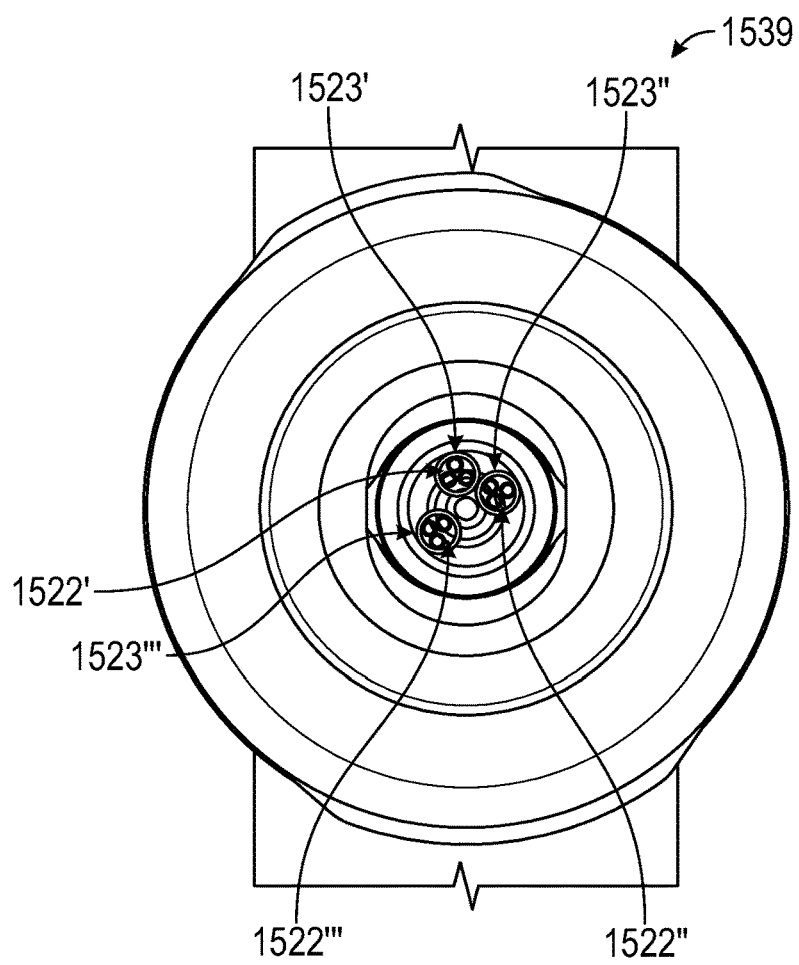

FIGS. 15A and 15B are proximal end views of the proximal region illustrated in FIG. 14, including three-port adaptor 1539, with FIG. 15B highlighting proximal ends of rails 1523 and fluid delivery lumens 1522 housed therein. FIG. 15A illustrates inflation port 1533 generally, guidewire lumen 1541 generally, and proximal ends of rails 1523 and fluid delivery lumens 1522 therein. FIG. 15B focuses on exemplary rails 1523', 1523", and 1523'''. In this example each rail 1523 houses therein three fluid delivery lumens, 1522', 1522", and 1522''', respectively. The fluid delivery lumens are in fluid communication with the needles, such that a therapeutic agent may be delivered into the proximal ends of the fluid lumens 1522 and to the needles. Any other feature from any other infusion devices herein may be incorporated into the example in FIGS. 15A and 15B, and vice versa.

Any of the needles may be deployable using an external component (that remains outside the patient) that is operatively coupled to one or more needles of the infusion device. In some exemplary embodiments, all of the needles in the infusion device are deployable in unison, and may be operatively coupled to a common deployment actuator, an example of which is shown in FIG. 14 and described above. It is understood that other mechanisms may be used to deploy the needles, either in unison or not in unison. For example, the external portion (which may be referred to herein as a proximal region of the infusion device) may have more than one actuator, each of which may control a subsection of the plurality of needles.

Any of the needles herein may be referred to as microneedles, and may be comprised of nitinol, stainless steel, and/or a combination of nitinol, stainless steel, and other materials that adapt the needle to be able penetrate into the vessel wall. Any of the needles herein may range in length from 0.1 mm-3 mm and in size from 20 gauge to 38 gauge, for example. For clarity, the lengths and/or size of individual needles may vary relative to any adjacent needles, either in the same spine or different spines. Furthermore, the relative inner diameter, outer diameter, and wall thickness of the individual needles may be uniform relative to adjacent needles, or they may vary relative to any adjacent needles, either in the same spine or different spines. Additionally, any of the needles herein may have at least one of an inner diameter ("ID") and an outer diameter ("OD") that varies along the length of the needle.

Any of the expandable infusion scaffolds herein may be configured to be an integral part of the balloon system. Alternatively, any of the expandable scaffolds herein may be configured as an independent structure that works 'in synergy' with a balloon-based system but is not attached to the balloon system and is not integral to such. As is described elsewhere herein, and incorporated into these embodiments, the expandable scaffold may take the form of various potential configurations designed to enable infusion lumen structural support and communication with the microneedles while also facilitating circumferential and longitudinal infusion of the intended agent to the target lesion.

In any of the infusion devices herein, the expandable infusion scaffold may comprise one or more infusion lumens extending in a longitudinal (axial direction; proximal-distal) or non-longitudinal pattern along at least a portion of the length of the balloon that is either integral to, or to be used in synergy with the infusion scaffold. Longitudinal in this context refers generally to at least a portion of an infusion lumen that is parallel with a longitudinal axis of inflatable balloon. In some embodiments, the scaffold may comprise one or more infusion lumens extending in a non-longitudinal pattern along at least a portion of the length of the balloon that is either integral to, or to be used in synergy with the infusion scaffold. Any of the infusion lumens herein may have one or more portions that extend longitudinally and one or more portions that extend non-longitudinally. Examples of a non-longitudinal configuration or pattern in this context include a spiral or helical configuration or other non-longitudinal pattern. For the sake of illustration, the following describes infusion lumens that run or extend longitudinally (axially) along at least a portion of the length of the scaffold. "Longitudinally" (and derivative thereof) and "axially" (and derivatives thereof) are generally used synonymously herein. "Linear" may also be used with longitudinal and axial when made in reference to a linear longitudinal or linear axial configuration, such as if parallel to a longitudinal (or long) axis of the infusion device or an inflatable member.

In some exemplary embodiments herein (such as in FIG. 6A-6F), the microneedles are secured (e.g., directly attached, or attached via one or more intermediate components) to a rail or other elongate member that is loaded into and disposed in the primary infusion spine. Exemplary benefits of this design include, but are not limited to, 1) protection of the balloon, guide catheter, delivery sheath, vessel wall, or any other structure in proximity to the microneedles by isolating the sharp needle points during delivery to the lesion site and/or removal from the lesion site; 2) the ability to use the scaffold to facilitate controlled dilation and optionally micro-penetration of the vessel wall ahead of deploying the infusion needles; and/or 3) added structural support during deployment of the needles. Needles that are secured to tracks or other elongate members herein may also enable the depth of needle deployment to be controlled or adjusted. For example, any of the rails herein may be in operable communication with an external portion (e.g., as shown in FIG. 13-15B), wherein one or more actuators (e.g., rotatable knobs, axially movable sliders) in the external portion may be adapted to be actuated to control the relative degree of motion of the rail track subassembly (e.g., axial translation), and thereby control the length of the needles that exit radially or somewhat radially outward from the infusion spine.

Any of the microneedles herein may also have one or more side holes or ports formed therein in addition to or alternatively to a port at a distal end of the needle. In variations of any of the embodiments herein, the needles may only have side holes and may not have a distal hole. Side ports or holes may enable concurrent infusion at more than one depth within the vessel wall. Exemplary benefits of having one or more side holes in the needle include, but are not limited to, enabling local delivery of the therapeutic agent or diagnostic agent into the medial layer of the vessel as well as deep into the adventitial layer of the vessel.

Any of the rails herein may also be referred to as a support shaft, any of which may be solid or have a lumen therein. The rails herein may be made of any number of potential materials such as nitinol or stainless steel onto which the needles can be bonded or attached (directly or indirectly), and which may optionally be slatted or laser cut along at least a portion thereof to provide enhanced trackability. Additionally, any of the rails herein may be comprised of more than one type of material along the length of the device. Any of the individual needles herein may include a first end that may be straight or linear and the other free end may be pre-formed (e.g., heat set) to take a perpendicular or near perpendicular configuration (e.g. 60-120 degrees) to the surface of the vessel when the needle is in its deployed state. A straight or linear section of a needle may be individually secured (e.g., directly attached) to an axially moveable member such as a rail, allowing the free end to be free to deform and assume its deployed shape (e.g., pre-set shape) as it exits the infusion spine opening.

Axial spacing between needles may be optimized based on the desired anatomical coverage of the agent within the vessel wall, along with spacing to facilitate optimal delivery and trackability of the infusion device to the target lesion.

In any of the embodiments herein, any number of distal ends of individual infusion spines (primary and optional secondary) may be axially staggered (or axially offset, or spaced axially) relative to any other infusion spine distal ends, further enhancing trackability of the distal end region of the device (an example of which is in FIG. 1). In any of the embodiments herein, at least two lumens may have distal ends that are axially aligned, but those distal ends may be axially spaced from one or more other infusion lumen distal ends. In this fashion, any number of infusion lumen distal ends may be axially aligned or axially staggered relative to any number of other infusion lumen distal ends. In the exemplary embodiment shown in FIG. 1, the infusion lumens are circumferentially staggered or off-set around or about the scaffold and inflatable member, as well as having distal ends that are axially offset such that the corresponding infusion needles are offset. In the exemplary embodiment shown in FIG. 5, the infusion lumens are circumferentially staggered or off-set around or about the scaffold and inflatable member, but axially aligned at the distal ends such that the corresponding infusion needles are axially aligned.

As described elsewhere herein, the individual rail remains inside the respective primary infusion spine, serving as a mechanism by which to advance and retract the microneedles. One or more openings (or windows) in the primary infusion spine provide guidance (or a pathway) for the microneedle(s) to exit the infusion spine and can also be adapted to function as added structural support as the needle penetrates into the vessel wall. Any of the infusion spine windows or openings herein (which may also be described as "space," and as such may be defined by surrounding structure in the infusion spine, for example) may be configured with a slight tented structure around the perimeter thereof to offer additional guidance and structural support, or they may be configured to be flat or concave relative to the cross-section of the infusion spine. The primary infusion spines herein may also be configured to have a structure located just distal or just proximal to an opening or window (the structure may define the surface(s) of the "opening") that is configured to function as an additional intraluminal guide or ramp as the needle advances out of the infusion spine opening.

In any of the examples herein, advancement and retracting of one or more rails or support shafts, to which one or more microneedles are secured (directly or indirectly), may be enabled through a mechanical turn dial (or any other rotatable handle actuator) or any other mechanical actuation mechanism with intuitive settings to guide the user during deployment and retraction of the microneedles.

In any of the examples herein, after the microneedles are deployed, infusion may be initiated using, for example only, a controlled mechanism of volume delivery based on the lesion length and desired volume of agent infused.

In any of the examples herein, the number of needles per primary infusion spine may be of any desired number, inclusive but not limited to the range of two to fifty microneedles per primary infusion spine. In some embodiments, the microneedles may be attached or otherwise secured by techniques such as welding, soldering, mechanical crimping, adhesive, or other techniques to a rail and/or fluid delivery lumen. The needles herein may be bonded directly to a fluid delivery lumen, or they be bonded to one or more intermediate elements such as a coupler. Further, as is described in more details elsewhere herein, the depth of needle deployment may be controlled or adjusted, for example, by utilizing one or more controls in an external portion of the device that may be adapted to control the relative degree of motion of the rail track or support shaft subassembly and thereby control the length of needle that exits radially or somewhat radially outward from the device.

In some examples herein, each needle associated with a primary spine is in fluid communication with an individual and separate fluid delivery lumen along at least a portion of the catheter length.

Figure 9:
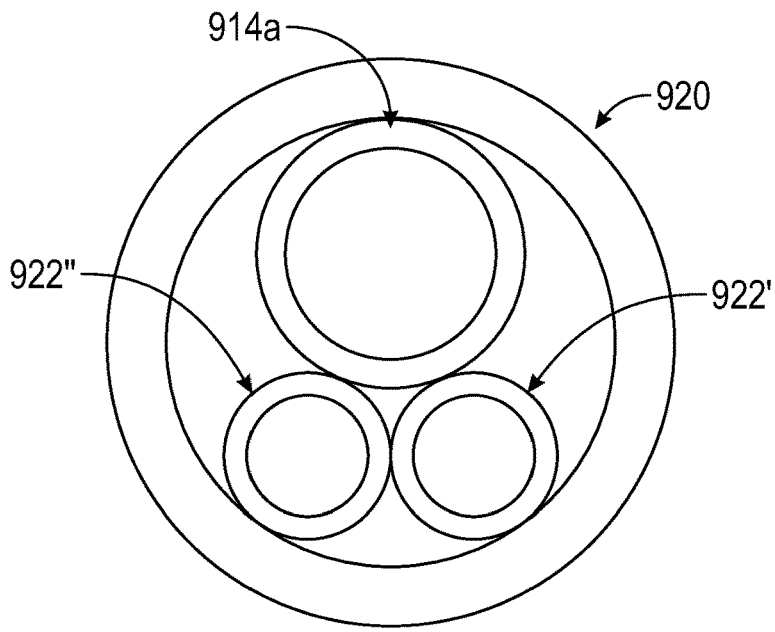
FIG. 9 illustrates an exemplary cross section of an exemplary needle or rail track subassembly.
Figure 10:
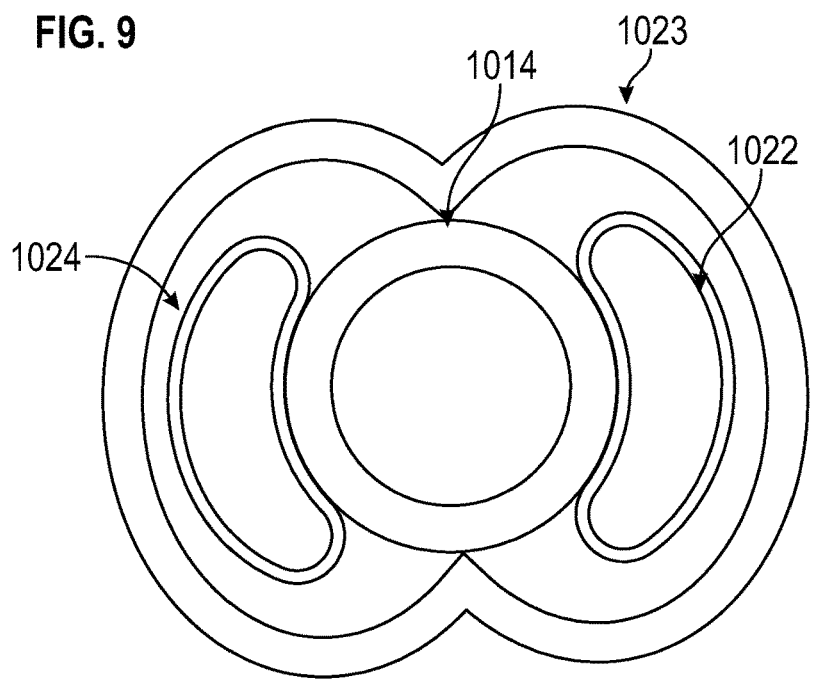
FIG. 10 illustrates an exemplary cross section of an exemplary needle or rail track subassembly.

Any of the fluid delivery lumens herein may have one of a variety of cross-sectional shapes inclusive of, but not limited to, round and kidney shaped. This may be done to help reduce the overall profile of the needle assembly without compromising the volume of agent that can be infused through the lumen(s). FIG. 10 is a sectional view through one of three needles associated with a particular spine (spine not shown for clarity). FIG. 10 shows exemplary rail 1023, exemplary needle 1014 and fluid delivery lumens 1022 and 1024 that are in fluid communication with a second and third needle, respectively, which are not shown as they are axially spaced from needle 1014. For example only, needle 1014 may be a proximal needle with two additional needles distal to needle 1014. In this example, rail 1023 is mechanically crimped and has a non-circular outer profile as shown. Fluid delivery lumens 1022 and 1024 have non-circular sectional shapes, which in this example can be approximated to kidney shaped, and may be crescent shaped in other embodiments. Alternatively, FIG. 9 illustrates a cross section of a rail track assembly 920 (920 is also pointing to the rail element) including needle 914a and fluid delivery lumens 922' and 922", wherein the cross section of the rail and the fluid delivery lumens are circular.

Any of the lumens herein may be comprised of one or more materials inclusive of, but not limited to, polyimide, polymer, nitinol, composite, and/or combination thereof. Any of the fluid delivery lumens and needles within a rail may be secured using a variety of potential techniques such as, without limitation, crimping, welding, soldering, potting, adhesive, or other techniques inclusive of a combination thereof. In any of these embodiments, any single needles may thus be in fluid communication with a unique or distinct fluid delivery lumen that is only in fluid communication with that particular needle and not any other needles. In alternatives, a plurality of needles may be in fluid communication with a first fluid delivery lumen, and a different needle may be in fluid communication with a second fluid delivery lumen.

In any of the embodiments herein wherein the expandable scaffold is attached to the inflatable member, the scaffold and/or individual spines may be bonded to the balloon or secured between the balloon and an additional thin walled layer of material, for example.

As disclosed elsewhere herein, in any of the embodiments herein, the infusion scaffold may be independent from the expansion balloon (not integrated therewith), yet is adapted to function in synergy with the expansion balloon. In these embodiments, the scaffold may be deployed prior to inflation of the balloon. For example, upon retraction of an outer scaffold sheath, the scaffold may be adapted to be self-expanding, partially self-expanding, or non-self-expanding. The expansion balloon may be then advanced within the scaffold and dilated to continue to or fully expand the infusion scaffold. The scaffold structure may be deployed passively by retracting an outer sheath (as would a self-expanding stent) or by a mechanical means activated in the handle of the device. The infusion scaffolds herein may be compatible with any off-the-shelf angioplasty balloon, and the balloon may optionally be drug-coated or uncoated. In some of these embodiments, the scaffold may be pre-loaded onto the expansion balloon (yet not attached thereto), with both delivered to the target lesion in unison, and the infusion scaffold may then be expanded as the dilatation balloon is expanded. The scaffolds herein may thus be at least partially deployed with an expansion balloon, but need not be bonded thereto.

In alternative examples, the scaffolds herein may be independent without the use of an expansion balloon. For example, the scaffold may be deployed into a target vessel and expanded radially. Radial expansion may be accomplished passively by retracting an outer sheath (as would a self-expanding stent that is commonly used in the field) and/or by a mechanical mechanism activated in the handle of the device. In an exemplary embodiment, the infusion scaffold is configured and adapted to be expanded using a mechanical mechanism or approach that compresses parts of the infusion scaffold longitudinally. The needles may then be advanced, as is described in more detail herein.

In some methods of use, the expandable scaffolds herein may be delivered about an inflatable member, either attached to the balloon or not. After the inflatable member and scaffold are delivered to the target location within a vessel, an inflation can be delivered to an inner volume within the inflatable balloon to cause its expansion. This balloon expansion applies a force to the expandable scaffold, causing the scaffold and spine to radially expand towards the vessel wall. The balloon can be expanded until the infusion device makes contact with the vessel wall. The needles may then be deployed from the spine opening and into the vessel wall, which is described in more detail elsewhere herein, and optionally by distally advancing one or more rails within the spines. The agent may then be delivered from a fluid source, through the one or more fluid delivery lumens, and out of the one or more needle ports and into the vessel wall optionally including the adventitia. The needles may be retracted by retracting one or more rails, and the scaffold and inflatable member may then be collapsed. The infusion device may then be recaptured (e.g., within a sheath or guide catheter) within a delivery sheath and removed from the patient or delivered to another location for a subsequent agent delivery process.

The disclosure that follows is also related to the disclosure above related to intravascular devices adapted and configured for delivery of a therapeutic and/or diagnostic agent into a wall of a target vessel of a human patient. Any of the suitably combinable disclosure from above may be incorporated into the devices and methods that follow.

As set forth above, while the primary spines and associated needles herein can be used to deliver a therapeutic agent relatively deep into the vessel wall (e.g., into the adventitia), it may also be beneficial to deliver an agent to less depth, such as onto the inner surface or into the intima of the vessel wall. The disclosure that follows facilitates delivery of one or more agents to different depth and into different layers of the vessel wall with the same device and without having to move the device within the vessel.

In some embodiments, the device comprises a scaffold that includes both primary openings, from which needles are deployed, and secondary openings, from which a secondary agent is delivered without use of a needle. The needles facilitate deeper delivery of a primary agent, while the secondary openings facilitate delivery of a secondary agent to the intima layer of the vessel wall. This facilitates two therapeutic approaches to different regions of the vessel. In some exemplary uses, an anti-restenosis primary therapeutic agent may be delivered deeper with the needles, while an anti-recoil secondary therapeutic agent, such as one or more vasodilators, may be delivered to less depth to the intimal layer of the vessel. The secondary agent may be adapted to treat elastic recoil of the vessel (e.g., acute) in response to deploying the devices herein into contact with the vessel wall. In some examples, needles may be used to deliver a primary agent deeper into the vessel wall for a first therapy, and a secondary agent may be delivered through secondary openings to a shallower location in the vessel wall to treat a more acute condition such as elastic recoil. Any of the primary agents herein (which are delivered through needles) may be the same as the secondary agent, or the primary agent may be different than the secondary agent.

Figure 17A:
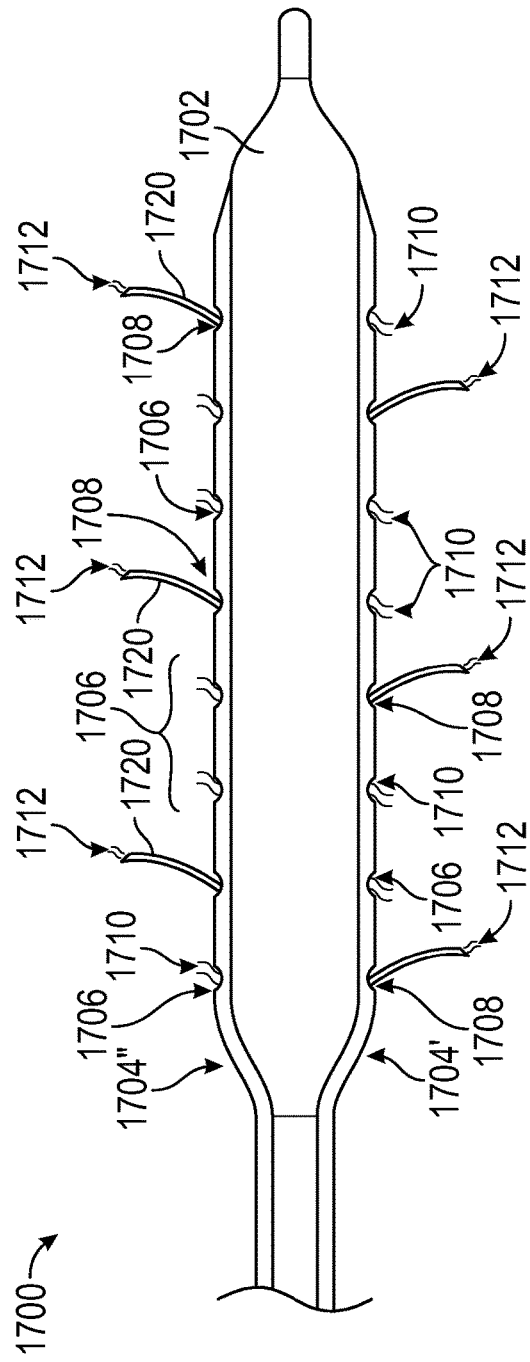
FIGS. 17A-17C illustrate side and end views, respectively, of an exemplary apparatus including a plurality of primary spines that comprise a plurality of primary openings and one or more secondary openings.
Figure 17B:
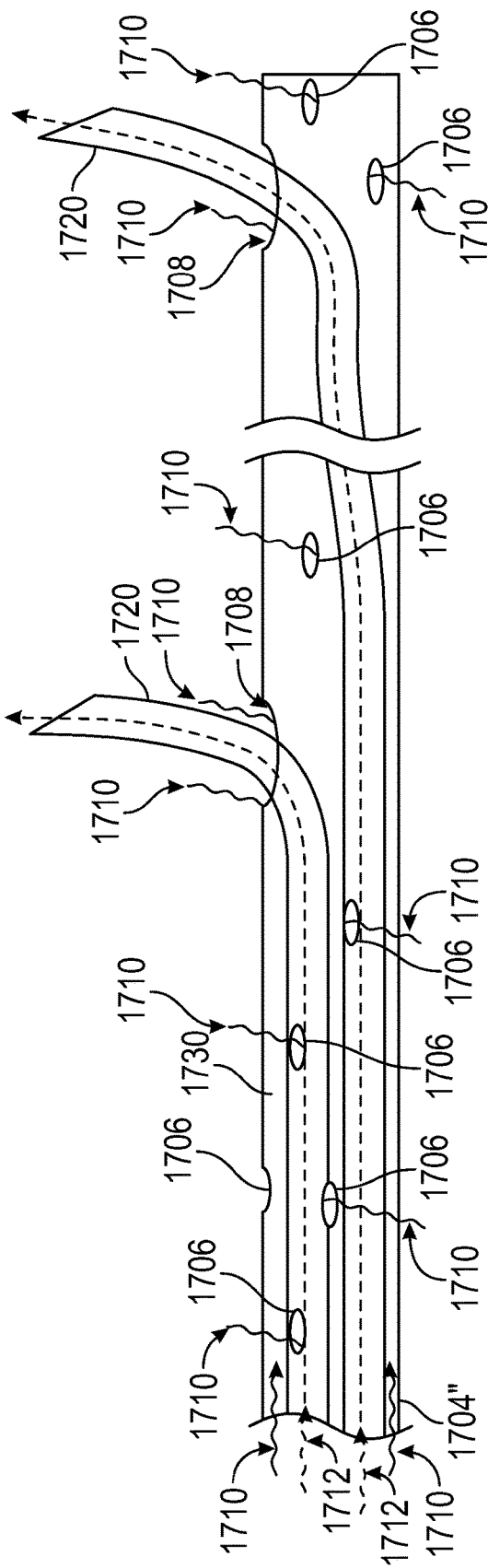
Figure 17C:
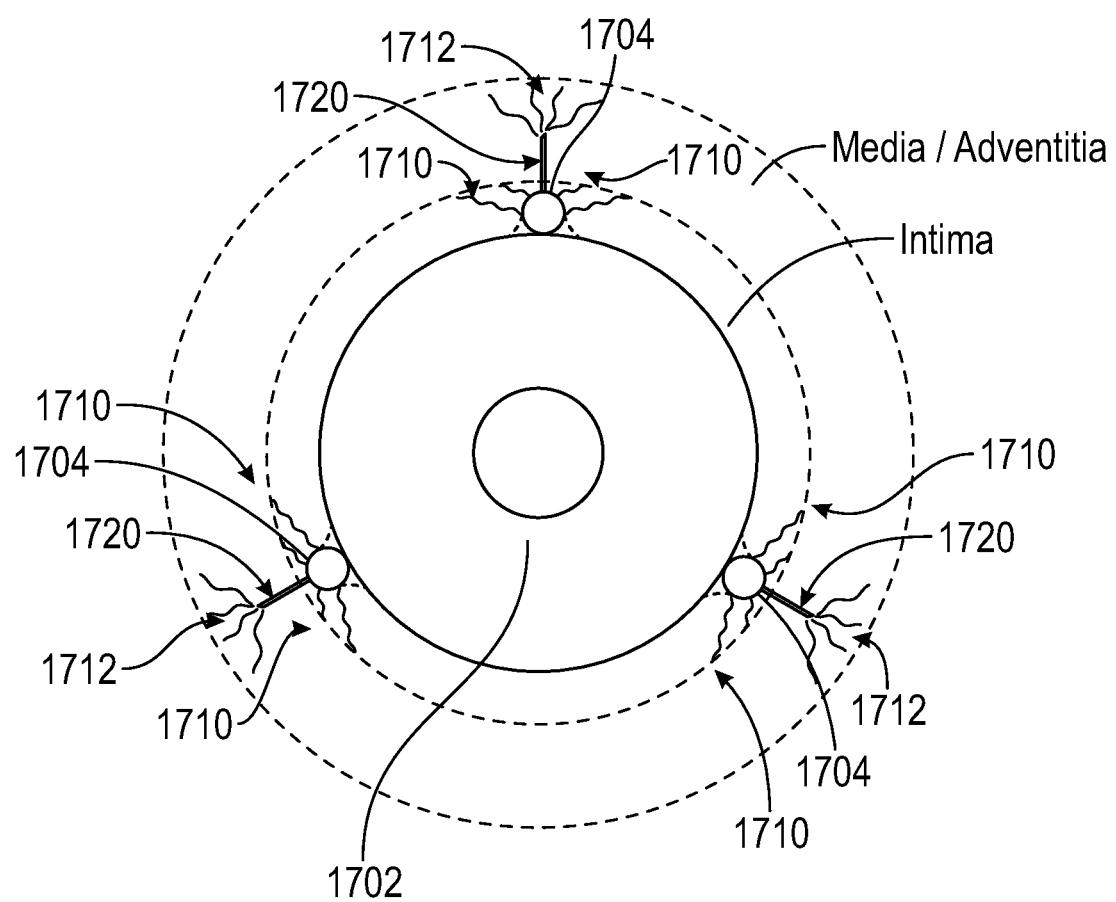

FIGS. 17A-17C illustrates a portion of exemplary intravascular apparatus 1700, which is shown with balloon 1702 inflated in a cylindrical configuration, and the expandable scaffold is expanded. The expandable infusion scaffold comprises one or more primary spines 1704' and 1704" that are disposed about the outer cylindrical surface of the inflatable balloon, as shown. The primary spines include a plurality of primary radial openings 1708 therethrough, each of the plurality of primary radial openings 1708 associated with a needle 1720 that has a delivery configuration (not shown in FIGS. 17A-17C) within the primary spine lumen 1730 of the primary spine (1704' and 1704") in which a distal tip of the needle is radially constrained by the primary spine, and a deployed configuration (as shown) in which the needle 1720 extends radially outward from the associated primary opening 1708 after the needle is advanced axially relative to the primary spine (1704' and 1704").

The one or more primary spines (1704' and 1704") further comprise one or more secondary openings 1706 therethrough that are not associated with a needle and are not adapted to deploy a needle therefrom. The one or more secondary openings 1706 are in communication with the primary spine lumen 1730 to facilitate delivery of a secondary agent 1710 from a proximal end of the apparatus, through the primary spine lumen 1730, and out of the one or more secondary openings 1706 into the intimal layer of the vessel wall.

Primary agent 1712 is shown being delivered from needles 1720, and secondary agent 1710 is shown being delivered from the one or more secondary openings 1706 as well as primary openings 1708. As shown in FIG. 17B, the primary agent 1712 is delivered through a fluid pathway that includes the needles 1720. As is also shown in FIG. 17B, secondary agent 1710 is delivered through primary spine lumen 1730, which in this embodiment is a space or volume between an inner surface of the spine and an outer surface of the needles.

As is described in more detail below, the secondary openings shown in FIG. 17B include some secondary openings that are both axially and circumferentially offset from one or more other secondary openings. Some of the secondary openings are circumferentially aligned, as shown.

Additionally, the secondary openings shown in FIG. 17B include some secondary openings that are axially offset from the primary opening 1708, as shown, and some secondary openings that are axially aligned with a primary opening. Some secondary openings shown in FIG. 17B are circumferentially aligned with the primary openings, while some secondary openings shown in FIG. 17B are circumferentially offset from the primary openings.

Any of the secondary openings 1706 may have the same relative positions in any of the secondary spines herein, with the understanding that the secondary spine would exclude any primary openings.

FIG. 17C illustrates an end view of device 1700 from FIGS. 17A and 17B, illustrating primary agent 1712 delivered from the needles 1720 and into the medial and/or adventitial layer of the vessel wall. Secondary agent 1710 is shown delivered through secondary openings 1706 (as well as through the primary openings) to expose the vessel wall to the secondary agent and in this example into the intimal layer of the vessel wall. As shown in FIG. 17B, secondary agent 1710 is delivered from primary spine lumen 1730 and through primary openings 1708, from which the needles are extending radially outward.

Figure 18:
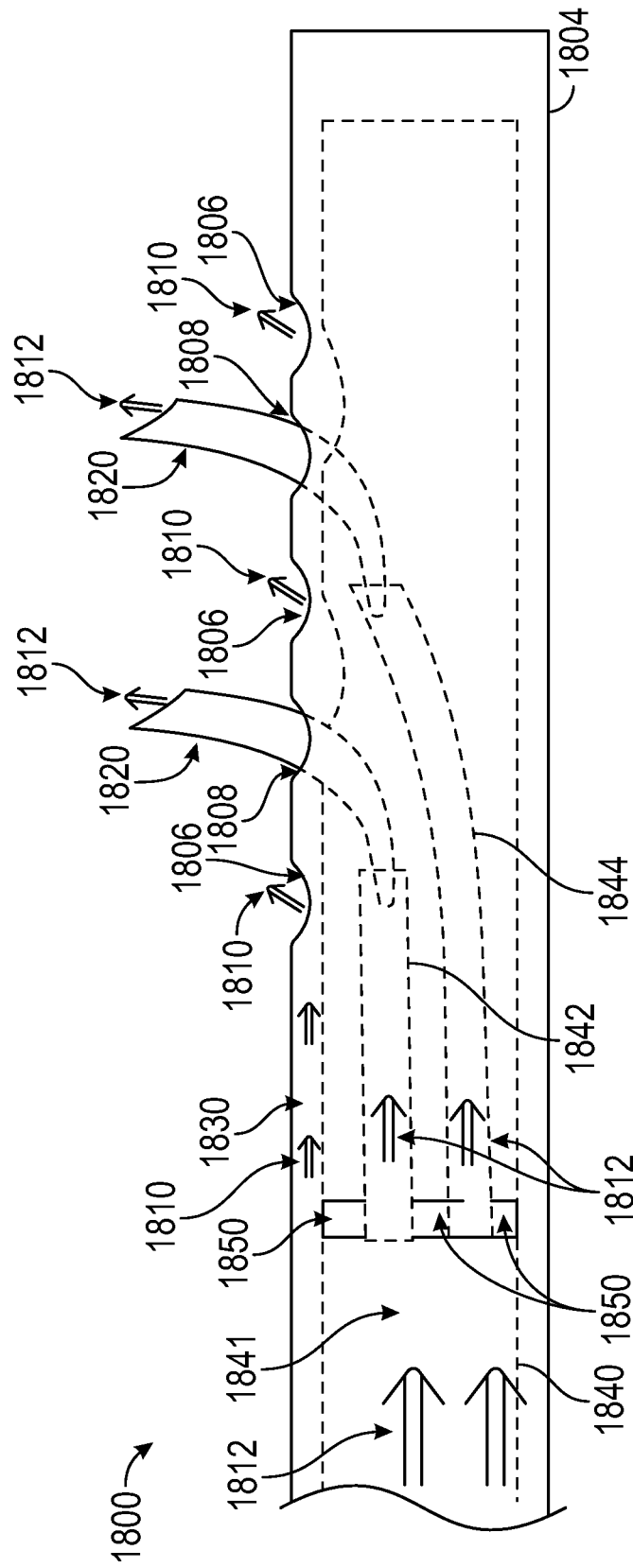
FIG. 18 illustrates an exemplary primary spine that comprise a plurality of primary openings and one or more secondary openings, and an exemplary axially movable rail assembly within the primary spine.

FIG. 18 illustrates a portion of exemplary intravascular apparatus 1800 that may incorporate any relevant disclosure from apparatus 1700 shown in FIGS. 17A-17C, including methods of use. Apparatus 1800 includes a rail 1840, examples of which are described elsewhere herein and are incorporated by reference herein to the disclosure of FIG. 18. Needles 1820 (shown deployed) are secured to rail 1840 such that they are adapted to be axially moved together relative to primary spine 1804. The apparatus also includes fluid lumens 1842 and 1844 that are in fluid communication with an individual needle, as shown. Proximal regions of the fluid lumens 1842 and 1844 are secured to rail 1840 with securing members 1850, which also act as a fluid barrier and direct primary agent 1812 from within rail lumen 1841 into the fluid lumens 1842 and 1844. Securing members 1850 may be any suitable material that is adapted to hold the fluid lumens in place and acts as a fluid barrier, such as, without limitation, a potting adhesive.

Secondary agent 1810 is delivered from a proximal end of the apparatus, through primary spine lumen 1830, and out of the one or more secondary openings 1806 to expose the vessel wall to the secondary agent. While not labeled in FIG. 18, secondary agent 1810 is also delivered out of primary openings 1808, from which needles 1820 extend radially (which is described and shown with respect to FIGS. 17A-17C). The primary openings 1808 are thus also in communication with fluid lumen 1830. In this example, primary spine fluid lumen 1830 is a space or volume at least partially defined by the inner surface of primary spine 1804 and an outer surface of rail 1840.

The primary spines herein may also include one or more secondary openings. FIGS. 19A-19D illustrate top views of merely exemplary positions of secondary openings relative to exemplary radial primary openings. Any of the relative positions in FIGS. 19A-19D may be incorporated into any of the primary spines herein.

Figure 19A:
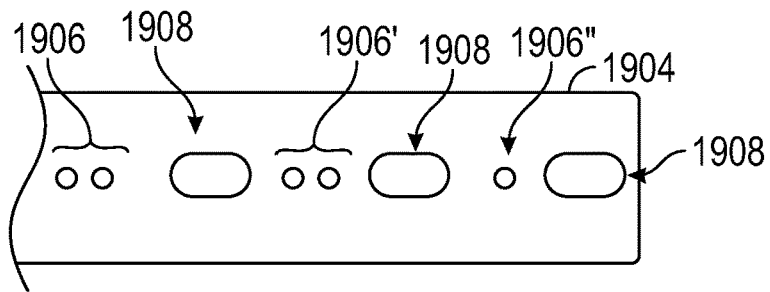
FIGS. 19A-19D illustrate exemplary primary spines with exemplary primary and secondary opening configurations and relative positions.

FIG. 19A illustrates a primary spine 1904, which includes a plurality of primary radial openings 1908, and a plurality of secondary openings 1906, 1906' and 1906", all of which are optionally circumferentially aligned with the plurality of primary openings 1908, as shown. Secondary openings 1906' are examples of a plurality of secondary openings that are axially in between adjacent primary openings, as shown.

Figure 19B:
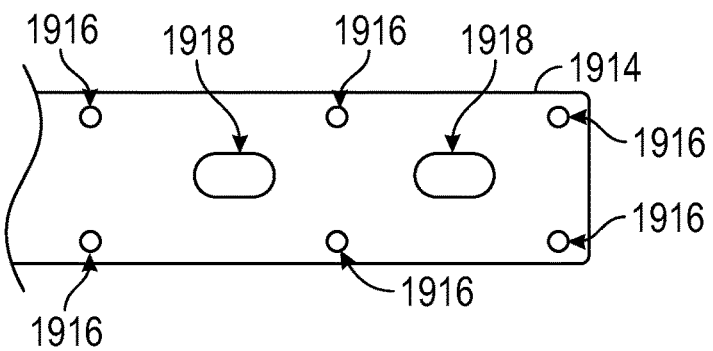

FIG. 19B illustrates exemplary primary spine 1914, which includes primary radial openings 1918 and secondary openings 1916, all of which in this example are circumferentially offset from primary openings 1918. Three of the secondary openings 1916 are shown circumferentially aligned with each other, and the other three of the secondary openings 1916 are circumferentially aligned with each other, as shown. Three pairs of the secondary openings 1916 are also axially aligned, as shown.

Figure 19C:
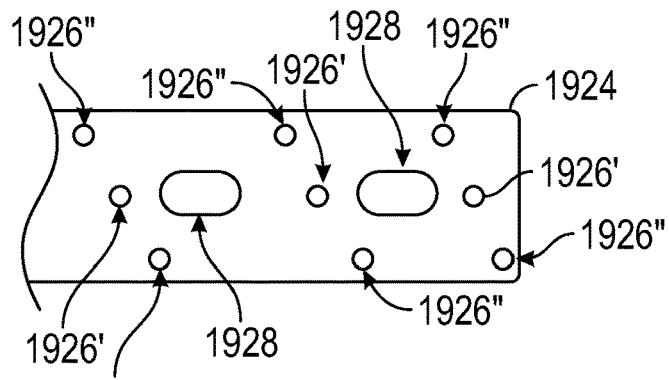

FIG. 19C illustrates exemplary primary spine 1924, which includes primary radial openings 1928 and secondary openings 1926' and 1926". Secondary openings 1926' are circumferentially aligned with but axially offset from primary openings 1928, as shown. Secondary openings 1926" are circumferentially and axially offset from primary openings 1928, as shown. The three groups of three secondary openings are shown to illustrate partial helical group configurations of at least three secondary openings.

Figure 19D:
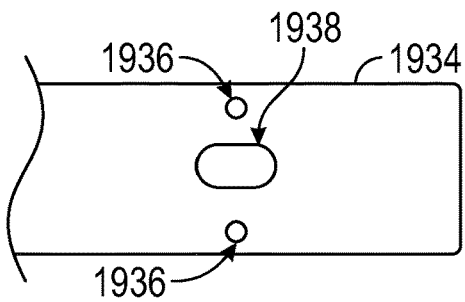

FIG. 19D illustrates exemplary primary spine 1934, which includes one or more primary radial opening 1938 (only one shown) and secondary openings 1936. Secondary openings 1936 are axially aligned with primary opening 1938 and circumferentially offset from primary opening 1938.

Any of the descriptions of the secondary openings in FIGS. 19A-19D can equally apply to secondary openings in any of the secondary spines herein, with the understanding that the primary openings in FIGS. 19A-19D would not be present in the secondary spine.

In any of the embodiments herein, any or all of the primary openings may be larger than one or all of the secondary openings, whether those secondary openings are in a primary spine or in an optional secondary spine. FIG. 17B is an example where primary openings 1708 are larger than secondary openings 1706. FIGS. 19A-19D is an example where the primary openings are larger than all of the secondary openings. In any of the embodiments, at least one of the one or more secondary openings may be the same size as at least one of the plurality of primary openings.

In any of the primary spines herein that include secondary openings, the number of secondary openings can be different than the number of primary openings, optionally greater than the number of primary openings. For example, the section of the device shown in FIG. 17B includes more secondary openings than primary openings. In some embodiments, the number of secondary openings may be the same as the number of primary openings.

The disclosure above describes spines that may be laser cut to impart flexibility along their lengths, which can increase flexibility for delivery. In some embodiments, the laser cuts in the spines may in fact constitute the one or more secondary openings in the spine, which allows the secondary agent to pass through the cut(s) and into the vessel wall. Laser cuts herein are examples of more generalized discontinuities in the wall of the spine, where the discontinuity is a secondary opening that facilitates weeping of the secondary agent therethrough.

Figure 21:
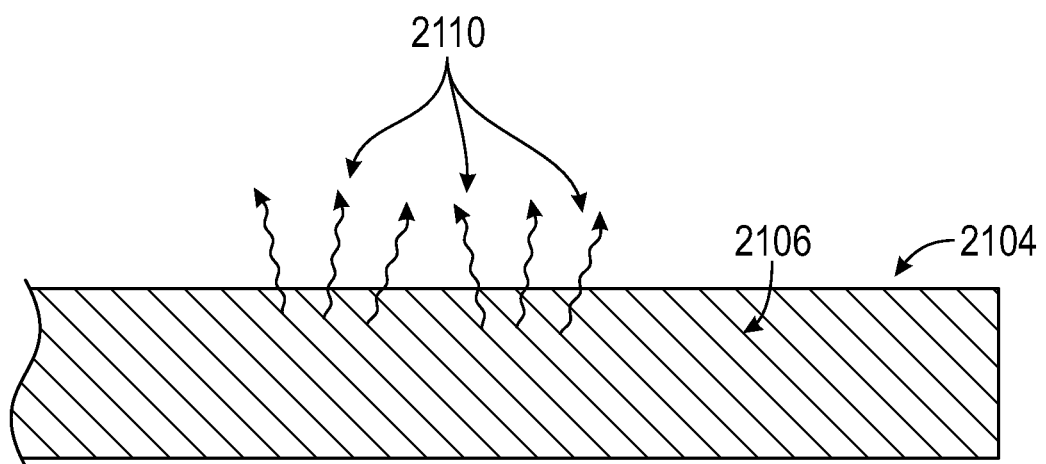
FIG. 21 illustrates an exemplary secondary or primary spine, with a discontinuity in the wall of the spine, wherein the discontinuity may facilitate delivery of a second agent out of the spine.

Both primary and optional secondary spines may include one or more discontinuities (e.g., one or more cuts therein) therein that are secondary openings. FIG. 21 is a side view of spine 2104 (which could be a primary or secondary spine) illustrating a secondary opening 2106 in the form of a laser cut helical pattern that facilitates delivery of secondary agent 2110 out of the spine 2104. In embodiments in which the spine has a laser cut pattern, part of the spine may be covered by a membrane to maintain fluid integrity, and the uncovered portion may act as the secondary opening. In these embodiments, the laser cut pattern may facilitate weeping of the secondary agent out of the secondary opening. In embodiments that include a laser cut pattern, a single, uninterrupted cut around the spine (e.g., in a helical configuration) may define a single secondary opening.

The needles may be adapted to be in communication with a first agent source outside the patient, and secondary openings may be adapted to be in communication with a second agent source outside the patient. The first and second sources may be the same sources, or they may be different sources. The different sources may contain therein the same agent or different agents.

Figure 20:
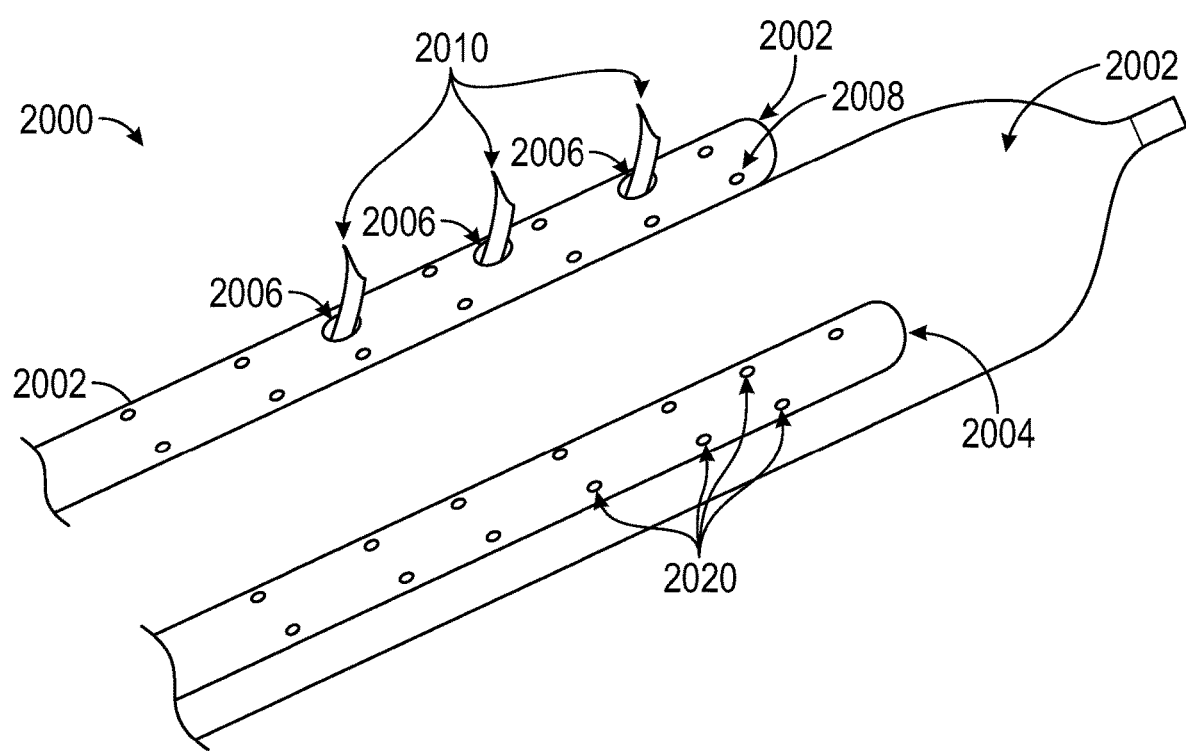
FIG. 20 illustrates an exemplary apparatus in an expanded configuration, the apparatus including one or more primary spines with needles deployed, and one or more secondary spines.

Any of the intravascular apparatus herein may also include secondary spine, which are spines that include one or more secondary opening and do not include openings from which a needle is deployed. FIG. 20 illustrates a distal end of intravascular apparatus 2000 where balloon 2002 is inflated to a cylindrical configuration and primary spine 2002 and secondary spine 2004 are disposed about an outer cylindrical surface of the balloon 2002.

Primary spine 2002 includes primary openings 2006, each of which is associated with a deployable needle as is described herein. Secondary spine 2004 includes one or more secondary openings 2022, which may have any of the relative positions described herein. In some alternatives, the one or more secondary openings 2020 may include a discontinuity in the spine 2004, such as a laser cut gap in the spine, examples of which are described herein.

FIG. 20 also illustrates optional secondary openings 2008 in primary spine 2002, which may be any of the one or more secondary openings herein. When optional secondary openings 2008 are not included in spine 2002, apparatus 2000 is an example of an apparatus with at least one primary spine without any secondary openings, and with at least one secondary spine.

One aspect of the disclosure herein is a method of intravascular fluid delivery and treatment, comprising: advancing an intravascular apparatus to a target location within a vessel; inflating a balloon toward a cylindrical configuration to cause one or more primary spines of an expandable infusion scaffold to expand toward a vessel wall and be disposed about an outer cylindrical surface of the balloon when the balloon is inflated, wherein the one or more primary spines include a plurality of radial primary openings and one or more secondary openings; moving a plurality of needles axially within the one or more primary spines and deploying the plurality of needles out of the radial primary openings such that tips of each of the plurality of needles pierce into the vessel wall; delivering a primary fluid agent out of the plurality of needles and into the vessel wall; and delivering a secondary fluid agent through a primary spine lumen and out of the one or more secondary openings to expose the vessel wall to the secondary agent.

The delivering steps may comprise delivering the primary fluid agent deeper into the vessel wall than the secondary fluid agent, such as into the adventitia with the secondary fluid agent exposed to the surface of the vessel wall and optionally to the intima.

In some embodiments delivering the primary fluid agent can comprises delivering an anti-restenosis agent out of the plurality of needles and into the vessel wall.

In some embodiments, delivering the secondary fluid agent can comprise delivering an anti-recoil agent out of the one or more secondary openings to expose the vessel wall (for example, at least the intimal layer) to the anti-recoil agent.

In some embodiments, the primary fluid agent may be the same as the secondary fluid agent.

The secondary and primary agents may be delivered at the same time, or at different times. In some uses, there may be some overlap in their deliveries, even if the deliveries are initiated at different times. In some embodiments, the primary agent may comprise more than one agent (e.g., two or more different therapeutics), which may be delivered simultaneously (e.g., in combination) or separately at different times.

In some embodiments, delivering the secondary agent out of the one or more secondary openings may be initiated before the plurality of needles are deployed from the radial primary openings. In some embodiments, delivering the secondary agent out of the one or more secondary openings may be initiated at a time subsequent to when the plurality of needles are deployed from the radial primary openings.

In some embodiments, delivering the secondary agent out of the one or more secondary openings is initiated at a time prior to delivering the primary fluid agent out of the plurality of needles.

In some embodiments, delivering the secondary agent out of the one or more secondary openings occurs while the primary fluid agent is being delivered out of the plurality of needles.

In some embodiments, delivering the secondary agent out of the one or more secondary openings is initiated at a time subsequent to delivering the primary fluid agent out of the plurality of needles.

In some embodiments, such as shown in FIG. 18, delivering a secondary fluid agent through a primary spine lumen comprises delivering the secondary fluid agent between an inner surface of the primary spine and an outer surface of an axially moveable rail to which the plurality of needles is secured. The primary agent may be delivered through a lumen of the rail before it reaches the plurality of needles.

The primary and secondary fluid agents may optionally be disposed in first and second fluid sources outside of the patient when in use and in fluid communication with the primary and secondary openings. The devices herein may be placed into communication with one or more agent sources prior to the procedure, and thus do not necessarily need to be in communication with the sources when packaged. This may allow one of several different agents and/or types of agents to be delivered with the fluid delivery devices herein.

The invention claimed is:

1. A method of intravascular fluid delivery and treatment, comprising:
   advancing an intravascular apparatus to a target location within a vessel;
   inflating a balloon toward a cylindrical configuration to cause one or more primary spines of an expandable infusion scaffold to move toward a vessel wall and be disposed about an outer cylindrical surface of the balloon,
      the one or more primary spines each including a plurality of radial primary openings through the primary spine and one or more secondary openings through the primary spine,
   at a time subsequent to inflating the balloon, moving a plurality of needles axially relative to and within the one or more primary spines and deploying the plurality of needles out of the radial primary openings such that tips of each of the plurality of needles pierce into the vessel wall;
   delivering a primary fluid agent out of the plurality of needles and into the vessel wall; and
   delivering a secondary fluid agent through a primary spine lumen and out of the one or more secondary openings to expose the vessel wall to the secondary fluid agent,
   wherein exposing the vessel wall to the secondary fluid agent comprises exposing an intimal layer of the vessel wall to the secondary fluid agent.

2. The method of claim 1, wherein delivering the primary fluid agent out of the plurality of needles and into the vessel wall comprises delivering the primary fluid agent into at least one of the media, adventitia, or perivascular layers of the vessel wall.

3. The method of claim 1, wherein the exposing step does not include exposing an adventitial layer to the secondary fluid agent.

4. The method of claim 1, wherein delivering the primary fluid agent comprises delivering at least one of an anti-restenosis agent or an anti-inflammatory agent out of the plurality of needles and into the vessel wall.

5. The method of claim 1, wherein delivering the secondary fluid agent comprises delivering at least one of an anti-recoil agent or an anti-thrombotic agent out of the one or more secondary openings to expose the vessel wall to the secondary fluid agent.

6. The method of claim 1, wherein the primary fluid agent is the same as the secondary fluid agent.

7. The method of claim 1, wherein delivering the secondary fluid agent out of the one or more secondary openings is initiated before the plurality of needles are deployed from the radial primary openings.

8. The method of claim 1, wherein delivering the secondary fluid agent out of the one or more secondary openings is initiated at a time subsequent to when the plurality of needles are deployed from the radial primary openings.

9. The method of claim 1, wherein delivering the secondary fluid agent out of the one or more secondary openings is initiated at a time prior to delivering the primary fluid agent out of the plurality of needles.

* * * * *